United States Patent
Ron et al.

(10) Patent No.: US 7,097,996 B2
(45) Date of Patent: Aug. 29, 2006

(54) METHODS OF SCREENING TEST COMPOUNDS USING GADD34L, AN EIF2α-SPECIFIC PHOSPHATASE SUBUNIT

(75) Inventors: David Ron, New York, NY (US); Céline Jousse, Saint Genes Champanelle (FR)

(73) Assignee: New York University, New York, NY (US)

( * ) Notice: Subject to any disclaimer, the term of this patent is extended or adjusted under 35 U.S.C. 154(b) by 333 days.

(21) Appl. No.: 10/650,482

(22) Filed: Aug. 28, 2003

(65) Prior Publication Data

US 2004/0142345 A1 Jul. 22, 2004

Related U.S. Application Data

(60) Provisional application No. 60/408,679, filed on Sep. 6, 2002.

(51) Int. Cl.
*C12Q 1/42* (2006.01)
(52) U.S. Cl. .......................................... 435/21; 435/375
(58) Field of Classification Search .................. 435/21, 435/375
See application file for complete search history.

(56) References Cited

U.S. PATENT DOCUMENTS 6,641,995 B1 * 11/2003 Brown et al. .................. 435/5

2003/0008272 A1 * 1/2003 Ron et al. ....................... 435/4
2003/0023872 A1 * 1/2003 Chen et al. .................. 713/200
2003/0032673 A1 * 2/2003 Nagy .......................... 514/557
2003/0219376 A1 * 11/2003 Fisher ........................ 424/1.49
2004/0023872 A1 * 2/2004 Brown et al. .................. 514/12

FOREIGN PATENT DOCUMENTS

GB 0 977 537 A2 * 5/2000
JP 2005-130744 * 5/2005

OTHER PUBLICATIONS

Harding et al., Mol. Cell 2000; 6: 1099-1108.
Harding et al., Nature 1999; 397: 271-74.
Harding et al., Mol. Cell 2000; 5: 897-904.
Novoa et al., J. Cell Biol. 2001 ; 153 : 1011-1022.

* cited by examiner

*Primary Examiner*—Ralph Gitomer
(74) *Attorney, Agent, or Firm*—Darby & Darby

(57) ABSTRACT

The invention is directed to methods and reagents for identifying test substances useful for the prevention or treatment of diseases involving an oxidative stress. The methods involve screening assays, including high throughput screening techniques, in which the test substances are tested for their ability to promote resistance to oxidative stress by inhibiting the activity of GADD34L, and thereby inhibiting the dephosphorylation of eIF2α, while not causing stress.

31 Claims, 11 Drawing Sheets

|  |  |
|---|---|
| 1 | ATTTTGGGCT TCGCTTCCAC CGCACCAGCC GGCCTACCCA GTCCTTCCGG TATCGCGTTG |
| 61 | CTCAGGGGCT TTTCAACCCT CTGTCAGTCG GAAAACCATC GCCGAGGCCG TGGGGGGACT |
| 121 | CCTATCCATG GTGTTGAAGC GTCGAGCCGA CTAGGGAACC TCCTTCCCCG CCAGGATGGA |
| 181 | AGTCGCATCA GTCGCCGCCT ATTGCGCGGG CTGTTCTTCC CTGTGTTCTG CCGCCCGCTG |
| 241 | CCGCATTCGC TGCCCTCTGT GGCTTTTCTG CTGGCTCGAA GATCGGCCTG GAGCAGCGAC |
| 301 | GCCACCGCTG GGCAAGGCCG AGACTCTGTA GGCTTCCTCC GAATCCCGTC GACCTCCAGC |
| 361 | CGCTGAGCGC CGCGGCCCTA CCTGAGAGAC TGTCAAGAAA AAGGAG<u>ATGG</u> AGCCGGGGAC |
| 421 | AGGCGGATCG CGGAAACGGC TTGGCCCTCG GGCGGGCTTC CGGTTCTGGC CACCCTTTTT |
| 481 | CCCTCGGCGA TCGCAAGCAG GCTCTTCTAA GTTCCGACG CCTCTTGGCC CGGAAAACTC |
| 541 | CGGGAACCCC ACACTGCTTT CCTCTGCCCA GCCGAGACT CGGGTCAGTT ACTGGACGAA |
| 601 | ACTGCTCTCC CAGCTCCTTG CGCCGCTCCC CGGATTGCTT CAGAAGGTGC TAATTTGGAG |
| 661 | CCAACTTTTC GGTGGAATGT TTCCGACCAG ATGGCTAGAT TTTGCTGGAG TCTACAGCGC |
| 721 | CCTGAGAGCC CTGAAGGGAC GGGAGAAACC AGCCGCCCCC ACAGCGCAGA AATCTTTGAG |
| 781 | TTCGCTGCAG CTCGACTCCT CAGACCCCTC GGTCACCAGT CCCCTTGATT GGCTAGAGGA |
| 841 | GGGGATCCAC TGGCAATACT CGCCCCCAGA CCTAAAATTG GAGCTTAAGG CCAAGGGAAG |
| 901 | TGCTTTGGAC CCTGCAGCAC AGGCTTTTCT CTTAGAGCAG CAGCTGTGGG GAGTGGAGCT |
| 961 | GTTGCCCAGT AGCCTTCAAT CCCGTCTGTA CTCTAACCGG GAACTTGGCT CTTCGCCCTC |
| 1021 | TGGGCCTCTA ACATTCAAC GCATAGACAA TTTCAGTGTG GTATCCTATT TGCTGAACCC |
| 1081 | TTCCTACCTG GACTGCTTTC CTAGGCTAGA AGTCAGCTAT CAGAACAGTG ATGGAAATAG |
| 1141 | CGAGGTAGTC GGCTTCCAGA CACTAACCCC AGAGAGCAGC TGCCTGAGAG AGGACCATTG |
| 1201 | TCATCCCCAG CCGCTGAGTG CAGAACTCAT TCCGGCCTCG TGGCAGGGAT GTCCACCTCT |
| 1261 | TTCTACGGAA GGCCTACCAG AAATTCACCA TCTTCGCATG AAACGGCTGG AATTCCTTCA |
| 1321 | ACAGGCTAAC AAGGGGCAAG ATTTACCCAC CCCTGACCAG GATAATGGCT ACCACAGCCT |
| 1381 | GGAGGAGGAA CACAGCCTTC TCCGGATGGA TCCAAAACAC TGCAGAGATA ACCCAACACA |
| 1441 | GTTTGTTCCT GCTGCTGGAG ACATTCCTGG AAACACCCAG GAATCCACTG AAGAAAAAT |

FIGURE 2A

```
1501  AGAATTATTA ACTACAGAGG TTCCACTTGC TTTGGAAGAA GAGAGCCCTT CTGAGGGCTG
1561  TCCATCTAGT GAGATACCTA TGGAAAAGGA GCCTGGAGAG GGCCGAATAA GTGTAGTTGA
1621  TTACTCATAC CTAGAAGGTG ACCTTCCCAT TTCTGCCAGA CCAGCTTGTA GTAACAAACT
1681  GATAGATTAT ATTTTGGGAG GTGCATCCAG TGACCTGGAA ACAAGTTCTG ATCCAGAAGG
1741  TGAGGATTGG GATGAGGAAG CTGAGGATGA TGGTTTTGAT AGTGATAGCT CACTGTCAGA
1801  CTCAGACCTT GAACAAGACC CTGAAGGGCT TCACCTTTGG AACTCTTTCT GCAGTGTAGA
1861  TCCTTATAAT CCCCAGAACT TTACAGCAAC AATTCAGACT GCTGCCAGAA TTGTTCCTGA
1921  AGAGCCTTCT GATTCAGAGA AGGATTTGTC TGGCAAGTCT GATCTAGAGA ATTCCTCCCA
1981  GTCTGGAAGC CTTCCTGAGA CCCCTGAGCA TAGTTCTGGG GAGGAAGATG ACTGGGAATC
2041  TAGTGCAGAT GAAGCAGAGA GTCTCAAACT GTGGAACTCA TTCTGTAATT CTGATGACCC
2101  CTACAACCCT TTAAATTTTA AGGCTCCTTT TCAAACATCA GGGGAAAATG AGAAAGGCTG
2161  TCGTGACTCA AGACCCCAT CTGAGTCCAT TGTGGCCATT TCTGAGTGTC ACACCTTACT
2221  TTCTTGTAAG GTGCAGCTGT TGGGGAGCCA AGAAAGTGAA TGTCCAGACT CGGTACAGCG
2281  TGACGTTCTT TCTGGAGGAA GACACACACA TGTCAAAAGA AAAAAGGTAA CCTTCCTTGA
2341  AGAAGTTACT GAGTATTATA TAAGTGGTGA TGAGGATCGC AAAGGACCAT GGGAAGAATT
2401  TGCAAGGGAT GGATGCAGGT TCCAGAAACG AATTCAAGAA ACAGAAGATG CTATTGGATA
2461  TTGCTTGACA TTTGAACACA GAGAAAGAAT GTTTAATAGA CTCCAGGGAA CATGCTTCAA
2521  AGGACTTAAT GTTCTCAAGC AATGTTGAGT TGGCAGCCTG TAGTCCTAGC TAGCATACAC
2581  TACCTCTTAC CTGAGAGGTG TCTTTTAAAA ACAAATCTTG GCAGCTGTCC TTTGACATTT
2641  TTTTTTTTAG AGGAAATGTA ACTTGGATCT AGTTTAATTT TTTTTTTTGC AACATATCCC
2701  ACTCAGAAAC ATTCAGGTTT GAAGCCAGCC CTGATAATGA AGGATGAACT AGTGTGATTT
2761  CTAATCCTCC CTTTTTTGAT TTAGTTGGAT GTGCTTTTAA ATGTCCTTTG CCTGCATGAG
2821  GTGGAAAGGG GACCTTTTTG AGTTGTCATT TTGCACTTTC AAAACTTATT TTCTTGGAAA
2881  ACAATATTTA TAGGGCTTAA AGCCCATTTT CATTTCTAAT CTAAATTATG TGTGCCTATC
2941  TG
```

FIGURE 2B

| | | | | | | |
|---|---|---|---|---|---|---|
| 1 | MEPGTGGSRK | RLGPRAGFRF | WPPFFPRRSQ | AGSSKFPTPL | GPENSGNPTL | LSSAQPETRV |
| 61 | SYWTKLLSQL | LAPLPGLLQK | VLIWSQLFGG | MFPTRWLDFA | GVYSALRALK | GREKPAAPTA |
| 121 | QKSLSSLQLD | SSDPSVTSPL | DWLEEGIHWQ | YSPPDLKLEL | KAKGSALDPA | AQAFLLEQQL |
| 181 | WGVELLPSSL | QSRLYSNREL | GSSPSGPLNI | QRIDNFSVVS | YLLNPSYLDC | FPRLEVSYQN |
| 241 | SDGNSEVVGF | QTLTPESSCL | REDHCHPQPL | SAELIPASWQ | GCPPLSTEGL | PEIHHLRMKR |
| 301 | LEFLQQANKG | QDLPTPDQDN | GYHSLEEEHS | LLRMDPKHCR | DNPTQFVPAA | GDIPGNTQES |
| 361 | TEEKIELLTT | EVPLALEEES | PSEGCPSSEI | PMEKEPGEGR | ISVVDYSYLE | GDLPISARPA |
| 421 | CSNKLIDYIL | GGASSDLETS | SDPEGEDWDE | EAEDDGFDSD | SSLSDSDLEQ | DPEGLHLWNS |
| 481 | FCSVDPYNPQ | NFTATIQTAA | RIVPEEPSDS | EKDLSGKSDL | ENSSQSGSLP | ETPEHSSGEE |
| 541 | DDWESSADEA | ESLKLWNSFC | NSDDPYNPLN | FKAPFQTSGE | NEKGCRDSKT | PSESIVAISE |
| 601 | CHTLLSCKVQ | LLGSQESECP | DSVQRDVLSG | GRHTHVKRKK | VTFLEEVTEY | YISGDEDRKG |
| 661 | PWEEFARDGC | RFQKRIQETE | DAIGYCLTFE | HRERMFNRLQ | GTCFKGLNVL | KQC....713 |

FIGURE 3

| | | | | | |
|---|---|---|---|---|---|
| 1 | CGGTCCTCCG | TCTCGCCCTG | CAGCTTCCGG | GTGTGCGGCT | GCGGCCATTT | TGAGCTTCGC |
| 61 | TTCTTTGCGC | CCTCGCCTGC | CACCCAGCCA | CCCTTTCCGC | CTTGGCGTTT | CGCGCCTCCG |
| 121 | TGCGGGCCAC | CGGAAACGCC | GCCGTCGTCT | CCGTCGCCGC | CGCGCGAGGG | AGGGTCTTCT |
| 181 | CTATGGTGGA | GCGATCTCAC | ACGGCCTAGG | ACGTCTCCTT | CCCTAGCCGG | GATGGACCTA |
| 241 | ACCGCGGTCG | CCACCGCTTG | CGCGGGCCTC | TGGGCCGTCC | GGTGCAGCAC | TCGTTGCGGA |
| 301 | AGCCGCCGCT | CTCTGGGCCT | CCTCTGCCGG | CGCGGGAATC | GGACTGCAGT | ACCCACTCCG |
| 361 | TGGCTGGGCA | AGGCGGAGAC | TGTGTAGACC | TCGGATCCAG | CCTGCGCTGA | CGCCGCTGAG |
| 421 | CTCTGTCCTC | CTCCTGTCTG | AGAAGCCGCC | AAGGAAAGGA | <u>GATG</u>GAGACA | GGAACGCACA |
| 481 | GGGCCCGGAA | GCGGCCTGGC | CCTCGGCTGG | GCTCCTGGTT | CCGGCTGCCC | TTCCTTCGGC |
| 541 | GATCGCACGC | CTGCTCTTCG | GAGTTCCCGC | CGCCTTCCTC | TCGACAAAAT | CCCGGGAACT |
| 601 | CCGCTCTGCC | CGAGCGTCGG | ACCAGGTACT | GGACCAAATT | GCTTTCTCAG | CTCCTTGCCC |
| 661 | TGCTCCCTAG | CCTATTCCAG | AAGCTGCTGC | TTTGGAGCCA | GCTTTCCGGG | GGCCTGATTC |
| 721 | CTACCAGATG | GCTAGATTTT | GCCGCAAGTT | ACAGCGCCCT | GAGAGCTTCG | AGAGGACGGG |
| 781 | AGGAATCTGA | CGCTCCCACG | GTGCAGAAGT | CTCTGAGTTA | CACTGCGGCT | GGACTCTTCG |
| 841 | CGAAGACTCG | CGTCGTCAGT | ACTCTTGCAT | GGCTAGAGG | AGGGACTCCA | GTGGCAGTGC |
| 901 | TCGTCCTCAG | ACTGGAAGTT | AAACTCAAGG | CCCAGGAAAG | AGCTTTAGAC | TCTGCAGCGC |
| 961 | CCACTTTCCT | CCTGGAGCAG | CAGCTGTGGG | GAGTGGAGTT | GCTGCCCAGT | AGCCTTCAAG |
| 1021 | CTGGTCTAGT | CTCCCACCGA | GAACTTGACT | CTTCATCCTC | TGGGCCTCTG | AGCGTTCAGA |
| 1081 | GCTTAGGTAA | TTTCAAGGTA | GTTTCCTATC | TCCTGAACCC | TTCCTACCTG | GACTACCTTC |
| 1141 | CCCAGTTAGG | GCTGCGCTGT | CAGAGCAGCG | CTGGAGGTGG | CCAGTTTGTG | GGTTTCCGAA |
| 1201 | CACTAACCCC | AGAGAGCTGC | TATCTTTCTG | AAGATGGTTG | TCACCCTCAG | CCGTTGCGGG |
| 1261 | CAGAGATGTC | GGCAACCGCC | TGGAGAAGGT | GTCCGCCTCT | CTCTACAGAA | GGCCTGCCGG |
| 1321 | AAATCCACCA | CCTTCGTATG | AAACGGCTAG | AATTCCTCCA | GGCTAACAAA | GGGCAAGAGT |
| 1381 | TACCCACCCC | TGACCAAGAT | AATGGCTATC | ATAGCCTGGA | GGAGGAACAT | AACCTTCTCC |
| 1441 | GGATGGACCC | ACAACATTGC | ACAGATAACC | CAGCACAGGC | GGTGTCCCCT | GCTGCAGACA |

FIGURE 4A

```
1501  GGCCGGAGCC CACTGAGAAA AAACCAGAAT TGGTGATTCA AGAAGTTTCA CAGAGCCCCC

1561  AGGGAAGCAG TCTGTTTTGT GAATTACCCG TGGAAAAAGA ATGTGAAGAG GACCACACTA

1621  ATGCAACTGA CCTCTCAGAT AGAGGAGAGA GCCTTCCTGT TTCTACCAGA CCAGTTTGTA

1681  GCAACAAACT GATAGATTAT ATTTTGGGAG GCGCCCCAG TGACTTGGAA GCCAGCTCTG

1741  ATTCTGAAAG TGAGGATTGG GGCGAGGAAC CTGAGGACGA TGGCTTTGAT AGCGATGGCT

1801  CCCTGTCTGA ATCAGACGTG GAACAGGACT CGGAAGGCCT TCACCTTTGG AACTCTTTCC

1861  ACAGTGTAGA TCCTTACAAA CCCCAAAACT TTACAGCCAC GATTCAGACG GCTGCCAGAA

1921  TTGCCCCCAG AGACCCATCA GATTCAGGGA CATCCTGGTC TGGCAGCTGT GGTGTAGGGA

1981  GCTGTCAGGA GGGACCCCTT CCGGAGACCC CCGACCATAG TTCCGGGGAG GAAGATGACT

2041  GGGAACCGAG TGCAGATGAA GCAGAGAATC TTAAATTGTG GAACTCTTTC TGTCATTCTG

2101  AGGACCCCTA CAACCTTTTA AATTTTAAGG CTCCTTTTCA ACCGTCAGGG AAGAATTGGA

2161  AAGGCCGTCA GGACTCAAAG GCCTCTTCTG AGGTCACAGT GGCCTTCTCT GGCCATCATA

2221  CCTTACTTTC TTGTAAGGCC CAGCTGTTAG AGAGCCAAGA AGATAATTGT CCAGGCTGTG

2281  GGCTGGGTGA GGCTCTTGCT GGAGAAAGAT ACACCCATAT CAAGAGAAAA AAGGTAACCT

2341  TCCTGGAAGA AGTTACTGAG TATTATATAA GTGGTGATGA GGATCGCAAA GGACCATGGG

2401  AAGAATTTGC AAGGGATGGA TGCAGGTTCC AGAAACGAAT TCAAGAAACA GAAGTTGCCA

2461  TTGGCTACTG CTTGGCCTTT GAGCACAGAG AAAAAATGTT TAATAGACTG AGGATCGAGT

2521  CAAAGGACTT ACTGTTGTAC AGCAATGTTA AGAAGTGAAC AGCCTGCAAC CCGTGCCCAC

2581  TCTGTCTCTT ACTTGAGAGT TTCCCTTAAA AACAAACACT GGCAGCTGTC CTTGGACATG

2641  TTTTTAAAGA AACAACTTGT ATCTAGAGAT GCAGTTTGAT TATTTTTGGG TAATGTGTCT

2701  CATTAGAAAC ACCAACTCCG ATAATGAAGA ATCTCTTATC TGTAATCCTC TCTTTTCCTA

2761  TTTAGTTGGA TGTGGGTTTT GTCTTTTTGA GAGGGTCTCA CTGCATAATT CTGTTTGGCC

2821  TAGGTCTATG TATGTAGACC AGGTTGGCCT TGAAGTTGGT ATTTCCTTGC CTCTGTTTCC

2881  TGTGCCACCA TGCCCAGCTG GAAGTGTTTT TAAATATCCT CTGCTTACCT GGGGTGAGAG

2941  TTTAATTTTG CACTTTCAAA ACGTTTCTTC TGGAGGCAGG GGCTGGTCTG GTTTACATAC

3001  AGGCTTCAGG CCAGCTAGGG CTATGTGGTG AGACCTAGTC TTAGAGGACA AACAGAACAA
```

FIGURE 4B

```
3061  AACAGTCAGG TTACTGTGGA AACTGAGGCA GGAGGATAGG AAGGTCCAGG TATGCCTGGA
3121  ACTCAGTGAA CTCTGAACTC AAGGCCAGCA TGGGGAGTTT AGCAAGACCT TTTTACACTC
3181  AGAATGGAAA AGGAAGCTGG GGATATAGCT CGGTAGCAGA GGCCCCTGCC TACATGTGCA
3241  AGGTCCTGGG TTCAGTCCCC AGTACTGCAA ATAGAAAGAA AAAACATTGT CTTGGATAAC
3301  TATAAGGTTT AAGCCTCATA GTCAGTTCTA ACTCAAATTA TGCATGCATT GAGTTCTTGT
3361  GTGCTTTTTC TGTTCTAAAA TTAATGGGCT TTATGGGTTT TGTTTTTGTA TGTTTTTATG
3421  TCTGTTATAT TTTGAGGTAG GGGATTGAGG CAGGGTCTCA CTGTGGCCTT GAGCTCATGG
3481  CAGTTTTCCT GCTTCAACTG AGTGTTTTGG TTTGTTTGTG TTTGTGTTTT TTTACTTTCA
3541  TAGATTTGAC TTAATGAAGG CAAAAACCTG TTATCAACCT AAAAGACATT GATGTGTCAC
3601  TTCAGTGGTG GATTTCTCC CTCTTTTTTT TTTTCCCCCA GAGCTGAGGA CCAAACCCAG
3661  GGCTTTGCAC TTGCTAGGCA AGCGCTCTAC CACTGAGCTA ATCCCCAAA CCACCCCCCC
3721  CCCTTTTCTT TTTTTAAAGA CATGGTCTTA TATAGTCTAG GCTGGCCTTA AACTCATTAC
3781  TTAGCCAAGG ATGGCTTTGA AAGATCCTCC TGTCCTCTTG TTTGGCTTGC ACATGGCATG
3841  TGCCATACAT CCAGATTTTT CTCTGTATCT AGGTCTTTTT AAGATATTTC CAAGGACTGC
3901  CCACAAATCC ACAGTGCAGT ACTTTCTTGA CTGGGAAAGC GGGGTTGGTG TGCTTTTCAA
3961  AGGCACACAC CATTATGCCC AGCTGGTCTG CCAAACTTAA CATATTTGGT TTCTGTGCAA
4021  ACTGTCCATT TGGAAGGTTT CTGTGTGTTG TAGTTTCAGT TGAATGTGGC TCTCTGTAGC
4081  TTTCAAGAAT GGGTAGAAAT CATAAAGCAC TCTTAAGTAA TCATTGCATT GTAGACATTT
4141  TTTTTTTTTA ACTAGGGGGT ATTTGGGAGA CATGTCAGAT ATTCACTTTT GTTTATGTG
4201  TCTTAAAACC AGTGTTACTT ACACCCTGCC TCAGCACTGG CACTTTTCAA ACCTGTCTTG
4261  GAGACACTGT AAACTTGGAT GGTGCAGTTC TGGGTTTTCA TGTGTAAAAT GTCAACTACA
4321  AAGGTCAATA TCCAGGTTTG TTGTGTTCTA CCTTATGTAG AGAGAAGCAA AGCAGAAAGG
4381  GCAGATAGAG CAGCCAGAAA GTGCTAGTGT CCCCCCCAAA GCGTGCTTCT AGATAGTGTG
4441  TGGATCAGGT GTGCTTGGTT TGTTCAGTTA GCGTCACCTG TTGTGCATGG TTGAGGTAAT
4501  GTGTTACCAG TTCTTTAGTG GTTACATGCA CAAAAGAGAG GACCTCTGAG TCGGGTGTGG
4561  GATGAGCTTT CCAGACCTGG CAGGGTAAAC TACCTCAGTT TATAATCTCC CTGGTTATTT
```

FIGURE 4C

```
4621  CCGTTTGATG TGATCTAAGG TCTGCCTCAG TGGTGATGAT GTTCATCCAC ACACAAGGTT
4681  AGTAAGAGTG CACGACCAGA AACGTTGGTC TTATTTTTGA GAACCCCCAT TTCTGTGTAT
4741  TTTATGCACC TGCCTTTAGT GAACTCCAGA GTGCATTAAA GAGTCTGGTT TAGTGCCGTG
4801  GGAATGGGCT AGTTTAGAAG CTATGTTTGG AAAGCAGGCA AGTTGACTTT AGGAAGAAAA
4861  GCTGTGACAG TGTGTAGACA TTTCTTTTAA ACCGGACTGC AGCTTAACAA CACTTGATTT
4921  CAGATGATTA GGTTTTGTT TCTGAGACCC AGCACCTGTA TATTTAAAAA TTGTTCCAGA
4981  TTACACCTTC ACTATCAAAT GAGTAAATGA CTCATGCCTG CAGACATGTC CTGATGGTGG
5041  CAAGAACAGA AGGATCTTTG ACTGAAGGAG AAAAACTGTC ATTGTCATCC CAGCCCCCAG
5101  GAAAGAACAC CTCCAAGGCA GGCAGGCAGG CAGGCAGGCA TGGTGGTTCT AGTTGAATAC
5161  ACATTCAAGT CTTGCAGTGG TGCTTTAGAT CTGTGTAGCA TGTGAGGCTC TGTACAGGTG
5221  GGGGCCACAC TTCTGAGGGC TGAAATGTGG CAACCCTTTA TCTAACTTGA AATCAAAACC
5281  GTCAAATTTT ATTTTTTATA ATTTAAGAAA GAGTTGGGGA ATGACATTTT TTGAGTTGGC
5341  CTTTTCAGCT CAGTCATTTT ACGTGTAACG TGGAGATTTG ATAGCTCAGA TTATATTTGT
5401  ATATAATTAT TAACTAATCT GTAAATTGTA ATAAATATAT TTGCAATTAT TAAAAAAAAA
5461  AAAAAAA.. 5468
```

FIGURE 4D

```
1    METGTHRARK RPGPRLGSWF RLPFLRRSHA CSSEFPPPSS RQNPGNSALP ERRTRYWTKL

61   LSQLLALLPS LFQKLLLWSQ LSGGLIPTRW LDFAASYSAL RASRGREESD APTVQKSLSY

121  TAAGLFAKTR VVSTLALARG GTPVAVLVLR LEVKLKAQER ALDSAAPTFL LEQQLWGVEL

181  LPSSLQAGLV SHRELDSSSS GPLSVQSLGN FKVVSYLLNP SYLDYLPQLG LRCQSSAGGG

241  QFVGFRTLTP ESCYLSEDGC HPQPLRAEMS ATAWRRCPPL STEGLPEIHH RRMRWLVFLQ

301  PNQGQDLPTL DQDNGYHSLE EEHNLLRMDP QHCTDNPAQA VSPAADRPEP TEKKPELVIQ

361  EVSQSPQGSS LFCELPVEKE CEEDHTNATD LSDRGESLPV STRPVCSNKL IDYILGGAPS

421  DLEASSDSES EDWGEEPEDD GFDSDGSLSE SDVEQDSEGL HLWNSFHSVD PYKPQNFTAT

481  IQTAARIAPR DPSDSGTSWS GSCGVGSCQE GPLPETPDHS SGEEDDWEPS ADEAENLKLW

541  NSFCHSEDPY NLLNFKAPFQ PSGKNWKGRQ DSKASSEVTV AFSGHHTLLS CKAQLLESQE

601  DNCPGCGLGE ALAGERYTHI KRKKVTFLEE VTEYYISGDE DRKGPWEEFA RDGCRFQKRI

661  QETEVAIGYC LAFEHREKMF NRLRIESKDL LLYSNVKK..698
```

METHODS OF SCREENING TEST COMPOUNDS USING GADD34L, AN EIF2α-SPECIFIC PHOSPHATASE SUBUNIT

This application claims priority to provisional U.S. application No. 60/408,679 filed Sep. 6, 2002 under 35 U.S.C. § 119(e), which is incorporated by reference.

This invention was made with Government support under Grant No. ES08681 awarded by the NIEHS and Grant No. DK47119 awarded by NIDDK. The United States Government may have certain rights to this invention pursuant to these grants.

Numerous references, including patents, patent applications, and various publications are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

FIELD OF INVENTION

The invention is directed to methods and reagents for identifying test substances useful for the prevention or treatment of diseases involving an oxidative stress. The methods involve screening assays, including high throughput screening techniques, in which the test substances are tested for their ability to promote resistance to oxidative stress by inhibiting the activity of GADD34L and thereby inhibiting dephosphorylation of eIF2α; in cells not subject to stress, while not causing stress.

BACKGROUND OF THE INVENTION

Primary reactive oxygen species (ROS), such as superoxide radicals, hydrogen peroxide, hydroxyl radicals, and ortho-quinone derivatives of catecholamines, exert their cellular effects by modifying DNA, lipids, and proteins to form secondary electrophiles. Examples of such secondary electrophiles include hydroxyalkenals, nucleotide propenals, and hydroxyperoxy fatty acyl chains. Secondary electrophiles are implicated in cellular dysfunction either because they are no longer able to participate in normal cellular activity or because they serve as electron acceptors in oxidative chain reactions that result in the modification of other essential cellular components. Damage caused by primary and secondary ROS contributes to the pathogenesis of several acute human diseases. ROS likely participate in the central nervous system damage caused by neuronal ischemia during stroke, post-cardiopulmonary bypass syndrome, brain trauma, and status epilepticus, as well as the cardiac damage induced during ischemic heart disease and renal damage induced by ischemia and toxins. ROS also likely participate in chronic human diseases such as the destruction of the islets of Langerhans of the endocrine pancreas in Diabetes Mellitus, the destruction of neurons in Parkinson's disease, and other chronic neurodegenerative disorders.

One way that cells handle the deleterious effects of ROS is via the preconditioning response, an adaptation whereby cells are rendered resistant to injury by prior exposure to smaller doses of the same ROS-inducing stress, which threatens to cause the injury in question. Thus, an ideal therapeutic strategy for the prevention and/or treatment of diseases involving an oxidative stress would involve stimulation of the preconditioning response without causing cellular injury. However, identification of potentially useful therapeutic agents has been hampered by the fact that compounds that cause the preconditioning response generally also cause stress to the cell.

Recently, the signaling pathways involved in the cellular response to oxidative stress have been elucidated (see FIG. 1). For example, the accumulation of malfolded proteins in the endoplasmic reticulum (ER stress) leads to accumulation of ROS. ER stress activates the protein kinase PERK, which in turn phosphorylates the translation initiation factor eIF2 on its alpha subunit [Harding, H., Zhang, Y., and Ron, D. (1999). Translation and protein folding are coupled by an endoplasmic reticulum resident kinase. Nature 397, 271–274]. A different eIF2α kinase, GCN2, phosphorylates eIF2α in response to nutritional stress [Harding, H., Novoa, I., Zhang, Y., Zeng, H., Schapira, M., and Ron, D. (2000). Regulated translation initiation controls stress-induced gene expression in mammalian cells. Mol. Cell 6, 1099–1108]. eIF2α phosphorylation leads to marked reduction in protein biosynthesis [Harding, H., Zhang, Y., Bertolotti, A., Zeng, H. and Ron, D. (2000). Perk is essential for translational regulation and cell survival during the unfolded protein response. Mol. Cell 5, 897–904] and to the expression of the transcription factor ATF4, which then activates stress response genes in a signaling pathway termed the Integrated Stress Response (ISR) [Harding, H., Novoa, I., Zhang, Y., Zeng, H., Schapira, M., and Ron, D. (2000). Regulated translation initiation controls stress-induced gene expression in mammalian cells. Mol. Cell 6, 1099–1108].

This activated Integrated Stress Response pathway is down-regulated by the activity of a phosphatase holoenzyme that dephosphorylates eIF2α on serine 51 (in yeast eIF2α, corresponding to residue 52 in rodents or humans). The phosphatase holoenzyme consists of the catalytic subunit of protein phosphatase 1 (PP1c) and GADD34, an eIF2α-specific regulatory subunit of the phosphatase [Novoa, I.; Zeng, H., Harding, H., and Ron, D. (2001). Feedback inhibition of the unfolded protein response by GADD34-mediated dephosphorylation of eIF2α. J. Cell Biol., 153, 1011–1022].

The expression of Integrated Stress Response target genes promotes resistance to both the stress of malfolded proteins in the endoplasmic reticulum and to the consequences of ROS accumulation. Methods to monitor activation of the Integrated Stress Response provide for effective screens to identify test substances capable of promoting preconditioning by activating the pathway in cells not subject to stress. Specifically, these screening methods to assess activation of the ISR provide the advantage of the identification of test substances, which activate the pathway, yet do not cause cell stress.

Substances that inhibit the eIF2α-specific phosphatase could promote the accumulation of phosphorylated eIF2α in cells not subject to stress, and thereby activate a protective ISR response without subjecting the cell to stress. Such substances would therefore be useful in the prevention and/or treatment of diseases involving an oxidative stress. GADD34 is limited in its use as a therapeutic target in this scheme as it is only expressed following stress-induced activation of eIF2α kinases, and not in cells not subject to stress. Therefore, inhibition of GADD34 is unlikely to provide a protective ISR response against oxidative stress in cells not subject to stress.

This invention involves the discovery of a GADD34-related regulatory subunit of PP1c, hereinafter referred to as GADD34-Like or GADD34L. Inhibition of GADD34L activity in cells not subject to stress leads to increased phosphorylation of eIF2α and to activation of the ISR. Therefore, GADD34L represents a useful therapeutic target for the promotion of preconditioning to prevent and/or treat diseases involving an oxidative stress. Furthermore, screening for test substances that are inhibitors of GADD34L activity provides the advantage of identifying therapeutic agents to prevent and/or treat diseases involving oxidative stress by activation of the ISR pathway, that do not provide cells stress.

SUMMARY OF INVENTION

This invention is thus directed to a method for screening a plurality of test substances useful for the prevention or treatment of a disease involving an oxidative stress, which comprises the steps of i) testing each of the test substances for its ability to inhibit the activity of GADD34L, and ii) identifying the test substance which inhibits the activity of GADD34L, thereby to identify a test substance useful as a preventive or therapeutic agent for a disease involving an oxidative stress. This invention is further directed to a method for identifying a test substance useful for the prevention or treatment of a disease involving an oxidative stress, which comprises testing a test substance for its ability to inhibit the activity of GADD34L, thereby to determine whether the substance promotes resistance to cell stress, and to identify said substance as a preventive or therapeutic agent for a disease involving an oxidative stress.

In one embodiment, the test substance promotes preconditioning and resistance to injury due to oxidative stress by inhibiting activity of the GADD34L protein. In a further embodiment, the test substance inhibits the association of GADD34L protein with the phosphatase PP1c. In another embodiment, the test substance inhibits the translation of GADD34L mRNA. In another embodiment, the test substance inhibits the transcription of the GADD34L genomic locus. In another embodiment, the method further comprises a step of verifying whether said test substance does not cause stress to cells. In a further embodiment, due to its effects on GADD34L, the test substance causes an accumulation of phosphorylated eIF2α in cells not subject to stress. In a further embodiment, due to its effects on GADD34L, the test substance inhibits dephosphorylation of eIF2α. In a further embodiment, due to its effects on GADD34L, the test substance activates the expression of Integrated Stress Response target genes. In a further embodiment, due to its effects on GADD34L, the test substance promotes cell survival following exposure to toxic concentrations of an agent which induces oxidative stress.

The invention is directed to a method for the prevention or treatment of a disease involving an oxidative stress in a patient in need of such treatment, which comprises administering to the patient an effective amount of a GADD34L phosphatase inhibitor identified for its ability to promote resistance to cell stress while not causing stress.

BRIEF DESCRIPTION OF THE FIGURES

FIGS. 2A and 2B: Full length human GADD34-Like (GADD34L) cDNA sequence (SEQ ID NO: 1). The open reading frame encoding the full length human GADD34L protein is encompassed by nucleotides 407 through 2548, inclusive. The start codon for the GADD34L protein is bold and underlined (ATG, FIG. 2A), while the stop codon is underlined (TGA, FIG. 2B). This sequence is identical to that of Genbank Accession Numbers NM_032833 and AK027650.

FIG. 3: Full length human GADD34-Like (GADD34L) amino acid sequence (SEQ ID NO: 2). This protein sequence is encoded by nucleotides 407 through 2545, inclusive, of the full length human GADD34L cDNA sequence (see FIGS. 2A and 2B). This sequence is identical to that of Genbank Accession Number NM_032833.

FIGS. 4A, 4B, 4C, and 4D: Full length mouse GADD34-Like (GADD34L) cDNA sequence (SEQ ID NO: 3). The open reading frame encoding the full length mouse GADD34L protein is encompassed by nucleotides 462 through 2558, inclusive. The start codon for the GADD34L protein is bold and underlined (ATG, FIG. 4A), while the stop codon is underlined (TGA, FIG. 4B).

FIG. 5: Full length mouse GADD34-Like (GADD34L) amino acid sequence (SEQ ID NO: 4). This protein sequence is encoded by nucleotides 462 through 2555, inclusive, of the full length mouse GADD34L cDNA sequence (see FIGS. 4A, 4B, 4C and 4D).

DETAILED DESCRIPTION OF THE INVENTION

Figure 1:
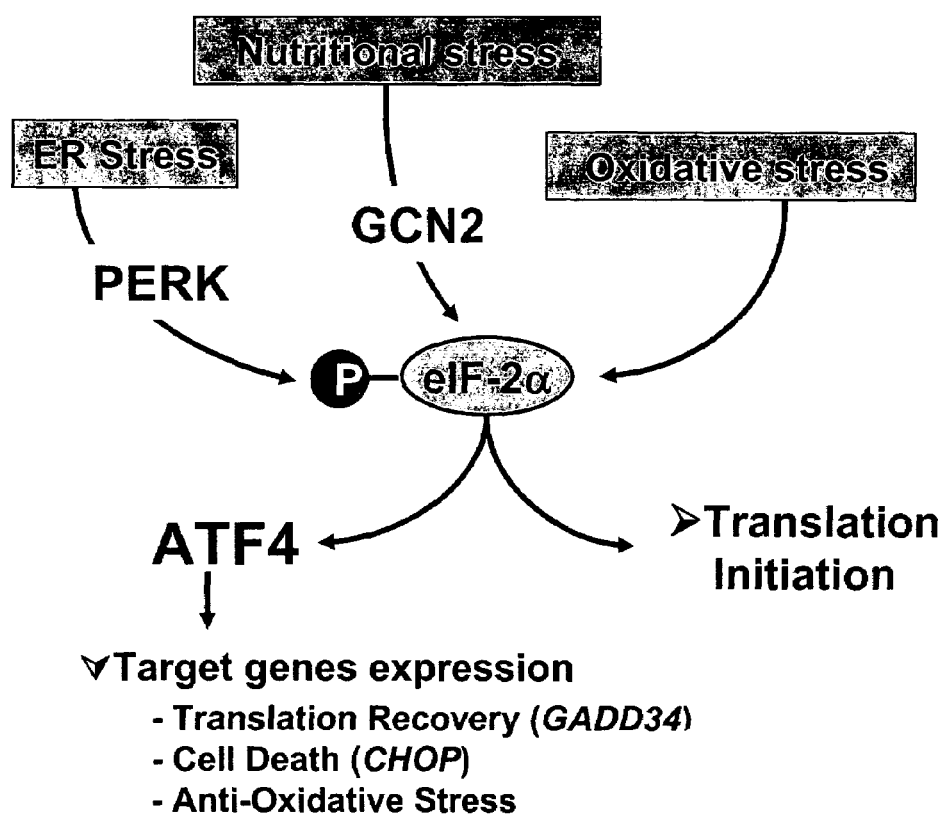
FIG. 1: A schematic description of a portion of the Integrated Stress Response (ISR). Kinases such as PERK and GCN2 respond to a variety of stresses by establishing a signaling pathway that converges on eIF2α phosphorylation. Phosphorylation of eIF2 on its α subunit represses translation of most mRNAs, while enhancing translation of special mRNAs such as ATF4. ATF4, a transcription factor, activates expression of various ISR target genes, including CHOP and GADD34. GADD34 encodes an eIF2α-specific regulatory subunit of the PP1c holophosphatase complex that terminates signaling in the ISR by dephosphorylating eIF2α.

Definitions:

The terms used in this specification generally have their ordinary meanings in the art, within the context of the invention, and in the specific context where each term is used. Certain terms are discussed below, or elsewhere in the specification, to provide additional guidance to the practitioner in describing the devices and methods of the invention and how to make and use them. For convenience, certain terms are highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to the preferred embodiments.

Primary reactive oxygen species (ROS) include, but are not limited to, superoxide radical, hydrogen peroxide, hydroxyl radical, and ortho-quinone derivatives of catecholamines. Primary ROS exert their cellular effects by modifying DNA, lipids and proteins to form secondary electrophiles. The secondary electrophiles are also implicated in cellular dysfunction either because they are no longer able to participate in normal cellular activity or because they serve as electron acceptors in oxidative chain reactions that result in the modification of other essential cellular components. Examples of such latter secondary electrophiles or secondary reactive oxygen species include hydroxyalkenals, nucleotide propenals, and hydroxyperoxy fatty acyl chains.

Oxidative stress or stressful conditions involves any actions by primary or secondary reactive oxygen species on the body.

Cell stress includes oxidative stress, ER stress, and nutritional stress on the cell and any subsequent cell injury due to the initial oxidative stress, ER stress, and nutritional stress.

Diseases involving an oxidative stress have a pathogenesis related to the damage caused by the primary and secondary ROS. ROS contribute to the pathogenesis of important human diseases caused by neuronal ischemia during stroke, post-cardiopulmonary bypass syndrome, brain trauma, and status epilepticus. ROS likely participate in cardiac damage induced during ischemic heart disease, renal damage induced by ischemia and toxins as well as in chronic diseases such as the destruction of neurons in Parkinson's disease, Amyloidoses, Prion disorders, Alzheimer's disease, and other chronic neurodegenerative disorders. Autoimmune diseases such as the destruction of the islets of Langerhans of the endocrine pancreas in Diabetes Mellitus are also encompassed.

Preconditioning is the effect in which a low dose of a stressful stimulus associated with oxidative stress promotes resistance to ROS. This effect is a natural cellular defense strategy to combat the effects of ROS.

Target gene and target protein are understood to refer to the gene or protein of the Integrated Stress Response pathway whose activation or inhibition is determined in the screening methods of the invention. The target genes or proteins are meant to refer to genes or proteins of any origin, regardless of the species. Substantially all the target genes or proteins used in the methods of the invention can be obtained from higher eukaryote organisms, such as mammalian or bird genes or proteins. They may more particularly be rodent or primate genes or proteins, preferably human. However certain of the genes or proteins used in the methods of the invention may alternatively be obtained from lower organisms such as yeasts. They may have homologous wild-type sequences or be function-conservative variants. Function-conservative variants are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A function-conservative variant also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

As used herein, the term homologous in all its grammatical forms and spelling variations refers to the relationship between proteins that possess a "common evolutionary origin," and homologous proteins from different species. Such proteins (and their encoding genes) have sequence homology, as reflected by their sequence similarity, whether in terms of percent similarity or the presence of specific residues or motifs at conserved positions. Accordingly, the term sequence similarity in all its grammatical forms refers to the degree of identity or correspondence between nucleic acid or amino acid sequences of proteins that may or may not share a common evolutionary origin. In a specific embodiment, two DNA sequences are substantially homologous or substantially similar when at least about 80%, and most preferably at least about 90 or 95%) of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system. Similarly, in a particular embodiment, two amino acid sequences are substantially homologous or substantially similar when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

A nucleic acid molecule is hybridizable to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaC1, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. In a specific embodiment, the term standard hybridization conditions refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Sequence-conservative variants are gene variants in which a change of one or more nucleotides in a given codon position results in no alteration in the amino acid encoded at that position.

Expression of a gene is understood to include both transcription and/or translation events.

A coding sequence or a sequence encoding an expression product, such as an RNA, polypeptide, protein or enzyme, is a nucleotide sequence that, when expressed, results in the production of that RNA, polypeptide, protein or enzyme; i.e., the nucleotide sequence encodes that RNA or it encodes the amino acid sequence for that polypeptide, protein or enzyme.

A promoter sequence is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently found, for example, by mapping with nuclease S1), as well as consensus sequences for protein binding responsible for the binding of RNA polymerase.

A coding sequence is under the control of or is operatively associated with transcriptional and translational control sequences in a cell when RNA polymerase transcribes the coding sequence into RNA, which is then spliced (if it contains introns) and, if the sequence encodes a protein, is translated into that protein.

The term transfection means the introduction of a "foreign" (i.e., extrinsic or extracellular) gene, DNA or RNA sequence into a eukaryotic host cell. The term transformation means the introduction of a "foreign" (i.e., extrinsic or extracellular) gene, DNA or RNA sequence into a prokaryotic host cell. In the case of both transfraction and transformation the host cell will express the introduced gene or sequence to produce a desired substance, in this invention typically an RNA coded by the introduced gene or sequence, but also a protein or an enzyme coded by the introduced gene or sequence. The introduced gene or sequence may also be called a "cloned" or "foreign" gene or sequence, may include regulatory or control sequences (e.g., start, stop, promoter, signal, secretion or other sequences used by a cell's genetic machinery). The gene or sequence may include nonfunctional sequences or sequences with no known function. A host cell that receives and expresses introduced DNA or RNA has been transformed and is a transformant or a clone. The DNA or RNA introduced to a host cell can come from any source, including cells of the same genus or species as the host cell or cells of a different genus or species.

The terms vector, cloning vector and expression vector mean the vehicle by which a DNA or RNA sequence (e.g., a foreign gene) can be introduced into a host cell so as to transform the host and promote expression (e.g., transcription and translation) of the introduced sequence. Vectors may include plasmids, phages, viruses, etc. and are discussed in greater detail below.

A cassette refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A large number of vectors, including plasmid and fungal vectors, have been described for replication and/or expression in a variety of eukaryotic and prokaryotic hosts. The term host cell means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g., a transgenic animal or a transiently transfected animal).

The term expression system means a host cell and compatible vector under suitable conditions, e.g. for the expression of a protein coded for by foreign DNA carried by the vector and introduced to the host cell. Common expression systems include E. coli host cells and plasmid vectors, insect host cells such as Sf9, Hi5 or S2 cells and Baculovirus vectors, Drosophila cells (Schneider cells) and expression systems, and mammalian host cells and vectors.

The term heterologous refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, a gene encoding a protein of interest, e.g., a GADD34L gene, is heterologous to the vector DNA in which it is inserted for cloning or expression, and it is heterologous to a host cell containing such a vector, in which it is expressed, e.g., a CHO cell. with a different gene that the one it is operatively associated with in nature.

The phrase cells that overexpress GADD34L, or portions thereof, is taken to indicate host cells of any type which have been transformed with an expression vector driving expression of exogenous GADD34L protein. The GADD34L protein expressed may represent a partial or complete GADD34L polypeptide as encoded by partial or complete GADD34L nucleic acid sequences within the expression vector. The GADD34L protein and nucleic acid sequences may be of mouse, human, hamster, or other mammalian origin. The GADD34L encoding sequences used may comprise function-conservative variants or sequence conservative variants of GADD34L. For use in the claimed methods, partial GADD34L polypeptides thus expressed must maintain partial or complete GADD34L activity as a suppressor of the Integrated Stress Response. Partial GADD34L polypeptides already defined which maintain such activity include: the C-terminal hamster GADD34L peptide encoded by the retroviral clone CD-GSE; the C-terminal mouse GADD34L peptide, comprising amino acids 418–698 of the full length protein, such as encoded in the expression construct pCMV2FLAG-ΔN GADD34L; and the N-terminally truncated mouse GADD34L peptide, comprising amino acids 24–698 of the full length protein, such as encoded in the expression construct pCMV2FLAG FL GADD34L.

Test substance or test compound is a chemically defined compound or mixture of compounds (as in the case of a natural extract or tissue culture supernatant) whose ability to promote resistance to cell stress, while not causing stress, is defined by the assays of the invention. These compounds or mixtures of compounds include, but are not limited to, chemicals including chemical libraries, peptides including peptide libraries, cDNA libraries such as retroviral cDNA libraries, phage display libraries, cell culture supernatants, cell extracts, and cell lysates.

The term therapeutically effective dose refers to that amount of a compound or compositions that is sufficient to result in a desired activity.

The phrase pharmaceutically acceptable refers to molecular entities and compositions that are physiologically tolerable and do not typically produce an allergic or similar adverse reaction (for example, gastric upset, dizziness and the like) when administered to an individual. Preferably, and particularly where a vaccine is used in humans, the term "pharmaceutically acceptable" may mean approved by a regulatory agency (for example, the U.S. Food and Drug Administration) or listed in a generally recognized pharmacopeia for use in animals (for example, the U.S. Pharmacopeia).

The term carrier refers to a diluent, adjuvant, excipient, or vehicle with which a compound is administered. Sterile water or aqueous saline solutions and aqueous dextrose and glycerol solutions are preferably employed as carriers, particularly for injectable solutions. Exemplary suitable pharmaceutical carriers are described in "Remington's Pharmaceutical Sciences" by E. W. Martin.

The terms about and approximately shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

General Methods

In accordance with the present invention, there may be employed conventional molecular biology, microbiology, and recombinant DNA techniques within the skill of the art. Such techniques are explained fully in the literature. See, for example, Sambrook, Fritsch & Maniatis, Molecular Cloning: A Laboratory Manual, Second Edition (1989) Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins, eds. 1984); Animal Cell Culture (R. I. Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994). Conventional techniques for in vitro cell culture and treatment, lysate preparation, immunoprecipitation, Western blotting, and immunodetection are also described in the art See for example, Harding, H., Zhang, Y., and Ron, D. (1999). Translation and protein folding are coupled by an endoplasmic reticulum resident kinase. Nature 397:271–274; Harding, H., Novoa, I., Zhang, Y., Zeng, H., Schapira, M., and Ron, D. (2000). Regulated translation initiation controls stress-induced gene expression in mammalian cells. Mol. Cell. 6:1099–1108; Harding, H., Zhang, Y., Bertolotti, A., Zeng, H., and Ron, D. (2000). Perk is essential for translational regulation and cell survival during the unfolded protein response. Mol. Cell 5:897–904; and Novoa, I.; Zeng, H., Harding, H., and Ron, D. (2001). Feedback inhibition of the unfolded protein response by GADD34-mediated dephosphorylation of eIF2α. J. Cell Biol., 153, 1011–1022.

The screening methods related to the Integrated Stress Response pathway are directed to different activation sites of the pathway, which includes, but is not limited to, the components illustrated in FIG. 1. The methods include:

1) Activated expression of Integrated Stress Response target genes included in Tables 1 and 2, ATF4, also known as CREB2, TAXREB67, and C/ATF4 (Harding, H., Novoa, I., Zhang, Y., Zeng, H., Shapira, M., and Ron, D. (2000). Regulated translation initiation controls stress-induced gene expression in mammalian cells. Mol. Cell 6, 1099–1108.), and of any target genes that can be identified by cDNA expression microarrays, that results from inhibition of the activity of GADD34L.

2) Increased phosphorylation of eIF2α [Harding, H., Novoa, I., Zhang, Y., Zeng, H., Schapira, M., and Ron, D. (2000). Regulated translation initiation controls stress-induced gene expression in mammalian cells. Mol. Cell 6, 1099–1108], caused by inhibition of the activity of GADD34L.

3) Inhibition of dephosphorylation of phosphorylated eIF2α. caused by inhibition of the activity of GADD34L.

These various endpoints can be measured by anyone skilled in the art of cell biology using the following methods.

Activation of expression of any target genes or proteins can be assessed by determining either the level of transcription or the level of translation, in the presence of test substance, in comparison with control assays performed in the absence of the test substance. Such assays may be performed on cells capable of expressing the target gene or a surrogate thereof, such as a reporter gene. The levels of phosphorylation of target proteins can be assessed by various methods, including immunoassays or radiolabeling.

TABLE 1

Target genes of the Integrated Stress Response identified by cDNA expression microarrays and Northern blot analysis

| Gene Name | Accession number (GenBank) |
| --- | --- |
| GLYT1 | W90900 |
| Cystathionine gamma-lyase | AA096870 |
| Methylenetetrahydrofolate dehydrogenase | W84014 |
| Serine Hydroxymethyltransferase | AA208877 |
| Heme Oxigenase-1 | AA213167 |
| XCTc | AA049696 |
| Coproporphyrinogen oxidase | AA259342 |
| CHOP | NM007837 |
| GADD34 | AA0050417 |

TABLE 2

Target genes of the Integrated Stress Response (Genes with statistically significant reduced ER stress inducibility in PERK mutant cells)

| Gene Name(s) | Product/homology | Putative/known functional category | Accession number (GenBank) |
| --- | --- | --- | --- |
| Tj6 | vacuolar ATPase, proton pump homologue | secreted pathway function | AA881202 |
| Sec23b | homologue of Sec23b SEC23B (*S. cerevisiae*) | secreted pathway function | AI848343 |
| Ugalt, Had1 | UDP-galactose translocator 2 | secreted pathway function | D87990 |
| 1500026A19Rik | dolichyl-phosphate beta-glucosyltransferase homologue | secreted pathway function | AA111463 |
| Gpnat1 | Glucosamine-phosphate N-acetyltransferase 1 | secreted pathway function | AW123026 |
| Pig-a | GPI-anchor biosynthesis (PIG-A protein) | secreted pathway function | D31863 |
| Sel1h | Sel1 (suppressor of lin-12) 1 homolog (*C. elegans*) | secreted pathway function | AF063095 |
| Sel11 | negative regulator of Notch, promotes ERAD | secreted pathway function | AW121840 |
| WRN typeII | Werner syndrome homologue; helicase | stress response | D86527 |
| A170, STAP | oxidative stress inducible | stress response | U40930 |
| p58, Prkri, mp58 | interferon inducible PKR inhibitor, DnaJ (Hsp40) | stress response | U28423 |
| p58, Dnajc3 | interferon inducible PKR inhibitor, DnaJ (Hsp40) | stress response | U28423 |
| Dnajb9 | DnaJ (Hsp40) homologue, subfamily B, member 9 | stress response | AW120711 |
| mATF4 | Activating transcription factor 4 | transcription/stress response | M94087 |
| LRG-21, ATF3 | Activating transcription factor 3 | transcription/stress response | U19118 |
| EST1 | alanine tRNA synthetase homologue | translation or amino acid metabolism | AI839392 |
| Wars | Tryptophanyl-tRNA synthetase | translation or amino acid metabolism | AI851163 |
| 1110068E11Rik | translation initiation factor eIF-4A -homologue | translation or amino acid metabolism | AW124530 |
| Rnu22 RNA | RNA, U22 small nucleolar | Ribosome biogenesis | AA684508 |
| GU2 | Nucleolar protein GU2, probable RNA helicase | Ribosome biogenesis | AA866971 |
| Snk | Serum-inducible kinase | signaling | M96163 |
| Fyn | proto-oncogene, tyrosine protein kinase | signaling | M27266 |
| 5730434I03Rik | BTF3 homologue (basal transcription factor) | transcription | AI846097 |

TABLE 2-continued

Target genes of the Integrated Stress Response (Genes with statistically significant reduced ER stress inducibility in PERK mutant cells)

| Gene Name(s) | Product/homology | Putative/known functional category | Accession number (GenBank) |
| --- | --- | --- | --- |
| Mpc2, Cbx4 | Chromobox homologue 4; transcriptional repressor | transcription | U63387 |
| Ets-2 | E26 avian leukemia oncogene 2, 3' domain | transcription | J04103 |
| c-myc | c-myc | transcription | L00039 |
| Arnt3, Bmal1 | CLOCK and NPAS2 dimer partner, regulated by NADH | transcription | AB014494 |
| E4BP4 | NFIL3/E4BP4 transcription, circadian rhythm regulated | transcription | U83148 |
| Etv6 | Ets variant gene 6 (TEL oncogene) | transcription | AI845538 |
| 2310004B05Rik | group XII secreted phospholipase A2 | secreted protein | AI845798 |
| EST2 | similar to extracellular matrix protein trichohyalin | secreted protein | AA612483 |
| Actb | Actb Actin, beta, cytoplasmic | cytoskelatin | M12481 |
| Ghitm | Growth hormone inducible transmembrane protein | growth/differentiation | AW120976 |
| EST3 | UCP2 mitochondrial uncoupling protein homologue | mitochondrial function | AW125634 |
| Rnula-1 | Small nuclear ribonucleoprotein polypeptide A | RNA/DNA housekeeping | L15447 |

Host Cells

A broad variety of host-expression vector systems may be utilized to express the coding sequences of the proteins used in the assays of this invention. These include, but are not limited to, mammalian cell systems such as Cos-7, CHO, BHK, 3T3, HEK293, HT22, and 293T cells. The mammalian cell systems may harbor recombinant expression constructs containing promoters derived from the genome of mammalian cells (e.g., metallothionein promoter) or from mammalian viruses (e.g., the adenovirus late promoter or the vaccine virus 7.5K promoter).

Additional host-expression vector systems include, but are not limited to, microorganisms such as bacteria (e.g., E. coli or B. subtilis) transformed with recombinant bacteriophage DNA, plasmid DNA, or cosmid DNA expression vectors containing PTK or adaptor protein coding sequences; yeast (e.g., Saccharomyces, Pichia) transformed with recombinant yeast expression vectors containing the protein or peptide coding sequences; insect cell systems, such as Sf9 or Sf21 infected with recombinant virus expression vectors (e.g., baculovirus) containing the protein or peptide coding sequences; amphibian cells, such as Xenopus oocytes; or plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the protein or peptide coding sequence. Culture conditions for each of these cell types is specific and is known to those familiar with the art.

In one example, COS-7 cells are grown on 150 mm plates in DMEM with supplements (Dulbecco's Modified Eagle Medium with 10% bovine calf serum, 4 mM glutamine, 100 units/ml penicillin/100 µg/ml streptomycin) at 37° C., 5% $CO_2$. Stock plates of COS-7 cells are trypsinized and split 1:6 every 3–4 days.

In another example, CHO cells are grown on 150 mm plates in HAM's F-12 medium with supplements (10% bovine calf serum, 4 mM L-glutamine and 100 units/ml penicillin/100 µg/ml streptomycin) at 37° C., 5% $CO_2$. Stock plates of CHO cells are trypsinized and split 1:8 every 3–4 days.

DNA encoding proteins to be assayed can be transiently or stably expressed in the cell lines by several methods known in the art, such as calcium phosphate-mediated, DEAE-dextran mediated, liposomal-mediated, viral-mediated, electroporation-mediated and microinjection delivery. Each of these methods may require optimization of assorted experimental parameters depending on the DNA, cell line, and the type of assay to be subsequently employed. In one embodiment, GADD34L protein, or portions thereof, may be expressed in cell lines using one or more of these methods.

In addition, native cell lines that naturally carry and express the nucleic acid sequences for the target protein may be used.

Activation of Target Genes

The screening of test substances may be assessed by determining either the level of transcription of the target genes or the level of translation of the target proteins encoded by the genes, in the presence of the test substance. These target genes are herein identified as genes whose expression is modified in response to an oxidative stress. They include the target genes of Table 1. The assays may be performed on cells capable of expressing the target gene or a surrogate thereof, such as a reporter gene.

Reporter gene assays of the invention may use one or more of the commonly used detection techniques involving isotopic, colorimetric, fluorimetric, or luminescent enzyme substrates and immuno-assay based procedures with isotopic, calorimetric, or chemiluminescent end points. The assays of the invention include, but are not limited to, using the reporter genes for the following proteins: CAT (chloramphenicol acetyltransferase), which transfers radioactive acetyl groups to chloramphenicol for detection by thin layer chromatography and autoradiography; GAL (β-galactosidase), which hydrolyzes colorless galactosides to yield colored products; GUS (β-glucuronidase), which hydrolyzes colorless glucuronides to yield colored product; LUC (luciferase), which oxidizes luciferin emitting photons; GFP (green fluorescent protein), which fluoresces on irradiation with UV; and hGH (human growth hormone), which is detected using a radioimmunoassay, and SEAP (a secreted form of the human placental alkaline phosphatase), which is detected with both calorimetric and chemiluminescent substrates.

Assays to monitor transcription of the target gene or the surrogate gene may be carried out by means of a Northern blot. Assays to monitor translation of the target gene or the surrogate gene may be carried out either by an immunoassay described herein or by utilizing the various read-outs for surrogate reporter genes described herein.

In one example, test substances, which inhibit the activity of GADD34L and in turn activate CHOP are assayed with a surrogate reporter gene. Chinese Hamster Ovary cells (CHO) are stably transfected with the GFP reporter gene fused to the CHOP gene to form a CHOP::GFP CHO cell line (Wang, X. Z., Harding, H. P., Zhang, Y., Jolicoeur, E. M., Kuroda, M., and Ron, D. (1998). Cloning of mammalian Ire1 reveals diversity in the ER stress responses. EMBO J. 17, 5708–5717). This cell line may be treated with test compounds and the activity of the marker gene, GFP, may be monitored to identify compounds, which activate the Integrated Stress Response. In another embodiment, by substituting a LUC or GAL reporter for the GFP reporter, stably transfected CHO cells may be adapted for use in high throughput screening of libraries of compounds.

In another example, translation of CHOP may be detected immunochemically in cultured cells exposed to test substances, by immunoblot or by immunocytochemistry described in the immunoassays herein, with antisera to CHOP as described in [Wang, X.-Z., Lawson, B., Brewer, J., Zinszner, H., Sanjay, A., Mi, L., Boorstein, R., Kreibich, G., Hendershot, L., and Ron, D. (1996). Signals from the stressed endoplasmic reticulum induce C/EBP homologous protein (CHOP/GADD153). Mol. Cell. Biol. 16:4273–4280]. The antisera to CHOP may also be adapted to an ELISA-based assay for measuring CHOP expression, allowing high throughput screening for compounds that promote CHOP translation.

In another embodiment, ATF4 translation may be detected by a surrogate assay using a stable cell line containing a reporter gene, such as LUC, controlled by the translational regulatory elements of the ATF4 mRNA (Harding, H., Novoa, I., Zhang, Y., Zeng, H., Schapira, M., and Ron, D. (2000). Regulated translation initiation controls stress-induced gene expression in mammalian cells. Mol. Cell 6, 1099–1108). The reporter gene is linked to all or part of the ATF4 promoter, in particular the ATF4 gene's translational regulatory sequences.

General Immunoassays

Various assays utilizing binding partners are useful in the screening methods of the invention. Preferably such binding partners are antibodies and the assays are called immunoassays. The below description refers to the use of antibodies, but it is understood that any other binding partner may be useful as well. Immunoassays are techniques known in the art, and include, for example, radioimmunoassay, ELISA (enzyme-linked immunosorbant assay), "sandwich" immunoassays, immunoradiometric assays, immunodiffusion assays, in situ immunoassays (using colloidal gold, enzyme or radioisotope labels, for example), western blots, precipitation reactions, immunofluorescence assays, and immunoelectrophoresis assays.

Monoclonal antibodies or polyclonal antibodies selective for the target protein are selected by techniques well known in the art. Immunoblots can be performed using lysates from cells that express the target protein to determine specificity. The preferred antibody will only bind to the target protein, preferably greater than 100,000 molecules per cell. An alternative method for determining specificity is immunoprecipitation. The binding affinity of the monoclonal antibody or polyclonal antibody for the substance can be determined by the relative strength of the signal generated in the immunoblot or by other techniques well known in the art.

A known number of cells expressing the target protein is lysed and serial dilutions of the lysate are applied to wells in a 96 well microtiter plate that have been precoated with the anchoring antibody. After allowing the substance to bind to the antibody, the unbound material is washed away and the amount of bound substance is determined using known immunoassay techniques. In order to have the proper signal to noise ratio one must be able to detect the target molecule in at least $1 \times 10^4$ cell equivalents per well. The maximum number of cells allowable per well is generally $<1 \times 10^5$ due to space constraints although this number may be somewhat larger or smaller depending on the cell type. The antibodies used in the immunoassays of the invention include, but are not limited to, polyclonal, monoclonal, chimeric, single chain, Fab fragments, and an Fab expression library.

For the production of antibodies, various host animals, including but not limited to rabbits, mice, rats may be immunized by injection with the particular antigen in a suitable adjuvant or by injecting the epitope conjugated to an immunogenic carrier. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies may be prepared by using any technique, which provides for the production of antibody molecules by continuous cell lines in culture. These include, but are not limited to, the hybridoma technique originally described by Koehler and Milstein, (Nature, 1975, 256: 495–497), the human B-cell hybridoma technique (Kosbor et al., 1983, Immunology Today 4:72) and the EBV-hybridoma technique (Cole et al., 1985, Monoclonal Antibodies and Cancer Therapy, Alan R. Liss, Inc., pp. 77–96). Human antibodies may be used and can be obtained by using human hybridomas (Cote at al., 1983, Proc. Natl. Acad. Sci. 80:2026–2030) or by transforming human B cells with EBV virus in vitro (Cole et al., 1985, in, Monoclonal Antibodies and Cancer Therapy, Alan R. Liss, pp. 77–96). Techniques developed for the production of "chimeric antibodies" (Morrison et al., 1984, Proc. Natl. Acad. Sci. 81:6851–6855; Neuberger et al., 1984, Nature 312:604–608; Takeda et al., 1985, Nature 314:452–454) by splicing the genes from a mouse antibody molecule of appropriate antigen specificity together with genes from a human antibody molecule of appropriate biological activity can be used; such antibodies are within the scope of this invention.

Techniques for the production of single chain antibodies (U.S. Pat. No. 4,946,778) can also be used to produce substance-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity to antigens. Antibody fragments which contain binding sites specific for the protein of interest may be generated by known techniques. For example, such fragments include but are not limited to: the F(ab')2 fragments which can be produced by pepsin digestion of the antibody molecule and the Fab fragments which can be generated by reducing the disulfide bridges of the F(ab')2 fragments.

The antibodies may be stored and purified using methods which are well known to those skilled in the art (e.g., see "Antibodies, A Laboratory-Manual", eds. Harlow & Lane, Cold Spring Harbor Laboratory, 1988, Ch. 8). Alternatively, polyclonal or monoclonal antibodies specific for the target protein may be obtained from commercial sources.

In the various immunoassays of the invention, antibody binding may be detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

The immunoassays of the invention may be carried out using an immobilized phase. Solid phases used for the immobilization of a protein may be prepared by coating with the specific antibody. In the case where a polyclonal antibody is used, the solid phase may first be coated with an anti-Ig that binds to the polyclonal antibody and indirectly immobilizes it to the solid phase. The solid phase may comprise a microtiter plate, a stick, tube, disc, fiber or the like, or a microtiter plate. A preferred solid phase is a 96 well microtiter plate such as those available from Coming, Cynatech, and Nunc. Particularly preferred 96 well plates are the Coming, Nunc MaxiSop, and Dynatech Immulon I and IV. Ideal conditions for maximum coating can vary with pH, ionic strength, and antibody concentration. Preferred conditions will be pH 6–9.5, 0–200 mM NaCl, and 1–10 µg/ml of antibody. Generally 150 µl per well is used. The antibody may be attached to the solid phase by any of a variety of methods known to those skilled in the art, including but not limited to non-covalent and covalent attachments.

The antibody may be labeled directly or can be detected using a secondary reagent. Such signal generating systems include, but are not limited to, enzyme-linked systems (such as horseradish peroxidase or alkaline phosphatase), radiolabels, fluorescent labels, light-emitting labels, light-absorbing labels, dyes, or biotin-avidin labeling systems (e.g., See "Antibodies, A Laboratory Manual, eds. Harlow & Lane, Cold Spring Harbor Laboratory 1988, Ch. 9).

In the case of conjugated enzymes, an appropriate substrate, such as a colorimetric substrate, is added. Specific substrates used for detection include ABTS (horseradish peroxidase), DAB, AEC, BCIP/NPT (alkaline phosphatase) and BCIG (beta-galactosidase). The binding of the enzyme-conjugated anti-IgG can be then detected quantitatively by techniques well known in the art.

Measure of Phosphorylation of eIF2α and the Activation of Kinases

The levels of phosphorylation of target proteins can be assessed by various methods, including immunoassays or radiolabeling. Specifically, the increase of phosphorylation of eIF2α may be measured, activation of the kinases that promote eIF2α phosphorylation may be assayed, and inhibition of dephosphorylation of phosphorylated eIF2α may also be determined by these techniques.

In a preferred embodiment, the level of phosphorylation of a protein is assessed by utilizing a binding partner, which should be highly specific for the target protein. It is preferred that the binding partner be an antibody. It is preferably generated against a unique epitope of the substrate. In an alternative, the binding partner should be specific for the phosphorylated form of the target protein. The detection procedure used to assess the phosphorylation state of eIF2α may for instance employ an anti-phosphoserine antibody or a peptide that recognizes and binds to phosphorylated serines. The detection antibody is preferably a polyclonal antibody to maximize the signal, but may also be specific monoclonal antibodies which have been optimized for signal generation.

In one example, levels of eIF2α phosphorylated on serine 51 (in yeast eIF2α, corresponding to residue 52 in rodents or humans) can be measured by immunoblot or immunocytochemistry utilizing a commercially available antibodies, for example, product #9721 from Cell Signalling Technology. In one embodiment, the commercially available antisera to phosphorylated eIF2α may be used to develop high throughput screening assays for test substances that promote the accumulation of phosphorylated eIF2α.

In another example, inhibition of dephosphorylation of eIF2α on serine 51 (in yeast eIF2α, corresponding to residue 52 in rodents or humans) may be assayed by screening a test substance's ability to inhibit the activity of the PP1c and GADD34L holophosphatase complex. The PP1c and GADD34L complex is active in vitro, and its activity may be reconstituted using recombinant proteins. A cell-free assay may be used with the PP1c/GADD34L complex in combination with phosphorylated eIF2α and test substances. By utilizing an ELISA assay, dephosphorylation of eIF2α by the PP1c/GADD34L complex, and inhibition of this dephosphorylation by a test substance, may be monitored by measuring the decrease in phosphorylated eIF2α signal.

In a further example, activation of the eIF2α kinases, PERK, GCN2, HRI, and PKR, may be measured. Activation of the kinases is associated with an autophosphorylation event on known residues in the kinase (e.g., threonine 898 of mouse GCN2 and threonine 980 of mouse PERK). By using antisera, which recognize the phosphorylated and activated forms of the kinases, activation of the kinases may be detected using immunoblot or immunochemistry, such as with an ELISA. Antisera for the phosphorylated forms of the kinases PERK and GCN2 have been developed. (Harding, H., Novoa, I., Zhang, Y., Zeng, H., Schapira, M., and Ron, D. (2000). Regulated translation initiation controls stress-induced gene expression in mammalian cells. Mol. Cell 6, 1099–1108).

Alternatively, immunoassays may be replaced by the detection of radiolabeled phosphate according to a standard technique. This involves incubating cells with the test substances and radiolabeled phosphate, lysing the cells, separating cellular protein components of the lysate using as SDS-polyacrylamide gel (SDS-PAGE) technique, in either one or two dimensions, and detecting the presence of phosphorylated proteins by exposing X-ray film.

The phosphorylation of a protein may also be conveniently detected by migration on an electrophoresis gel and Western blot, to thereby observe whether a shift of the molecular weight of the protein occurs, a phosphorylated protein being heavier than the corresponding non-phosphorylated form.

Assays to Exclude Test Substances that Cause Stress

The above assays may be utilized to establish the site of action of the test substances. However, additional steps of verifying whether the test substances do not cause stress to the cells can be contemplated. For that purpose, one can measure the level of activation of other signaling proteins activated by ER stress, but not involved in the preconditioning pathway. More particularly, one can measure the level of phosphorylation of IRE1 (Bertolotti, A., Zhang, Y., Hendershot, L., Harding, H., and Ron, D. (2000). Dynamic interaction of BiP and the ER stress transducers in the unfolded protein response. Nature Cell Biology 2, 326–332; Harding, H., Zhang, Y., Bertolotti, A., Zeng, H., and Ron, D. (2000). Perk is essential for translational regulation and cell survival during the unfolded protein response. Mol Cell 5, 897–904), utilizing any standard method such as an immunoassay using an antibody specific for the phosphorylated form of the protein. One can also measure the cleavage of the protein called ATF6 (Wang, Y. et al., J. Biol. Chem., 2000, 275(35), 27013–27020), for example by tracking the appearance of the cleaved shorter forms of the protein on a Western blot.

In the case wherein the test substance causes ER stress. This may be assayed by measuring the level of activation of other signaling proteins activated by ER stress, as mentioned herein, or by measuring the level of expression of BiP. Specifically, either the level of transcription or the level of translation of this chaperone protein is assessed. An increase in the level of expression of BiP is indicative of a stress, and therefore the test substances that promote such increases may be discarded as undesirable.

One may also assess whether the test substances promote the uncharging of tRNAs, another undesirable consequence of cell stress. Established methods may be used (Dudek, S. M. et al., J. Biol. Chem., 1995, 270(49), 29323–29329). Specifically, the assay involves isolating tRNA, a fraction of which is charged with an amino acid and a fraction of which is not. One aliquot is oxidized, which prevents any initially uncharged tRNA from subsequently being acylated with an amino acid. Oxidation does not affect the ability of initially charged tRNA to be reacylated in vitro after the attached amino acid is removed, because the presence of the amino acid protects the 3' terminus of the tRNA from damage by periodate. A second aliquot is left unoxidized, allowing the determination of the total charging capacity of tRNA. The percentage of charged tRNA is determined by dividing the counts from in vitro charging reactions (using radiolabeled amino acids) using oxidized samples by the counts from reactions using unoxidized samples.

High throughput Screening

The above assays may be performed using high throughput screening techniques for identifying test substances for developing drugs that, when added to cells, promote resistance to ROS without causing stress themselves. High throughput screening techniques may be carried out using multi-well plates (e.g., 96-, 389-, or 1536-well plates), in order to carry out multiple assays using an automated robotic system. Thus, large libraries of test substances may be assayed in a highly efficient manner.

A preferred strategy for identifying test substances starts with cultured cells that overexpress GADD34L, or portions thereof, and are transfected with a reporter gene fused to the promoter of any gene that is activated by the stress response pathway. More particularly, stably-transfected CHO cells growing in wells of micro-titer plates (96 well or 384 well) can be adapted to high through-put screening of libraries of compounds. The CHOP promoter is a preferable promoter due to its low basal activity. Libraries of test substances may be screened using this strategy. For example, the DIVERSE™ library of universally diverse, pre-designed 10,000–50,000 drug-like small molecules (ChemBridge Corporation, San Diego) may be used. Compounds in the library will be applied one at a time in an automated fashion to the wells of the microtitre dishes containing the transgenic cells described above. A compound that inhibits the activity of GADD34L and consequently activates the reporter driven by the CHOP promoter will be identified and this particular compound will be subjected to secondary testing in one or all of the assays described herein. The composition and the structure of the identified test substances will be determined by referring back to the ChemBridge database. The test substance may be developed into a therapeutic agent to prevent or treat a disease caused by oxidative stress.

The ELISA assay for measuring phosphorylated eIF2α, by means of commercially available antiserum, may be developed for high throughput screening. ELISA-type assays may be performed in microtitre plates. See, for example, Peraldi et al., 1992, J. Biochem. 285: 71–78; Schraag, et al., 1993, Analytical Biochemistry 211: 233–239; Cleavland, 1990, Analytical Biochemistry 190: 249–253; Farley, 1992, Analytical Biochemistry 203: 151–157; and Lczaro, 1991, Analytical Biochemistry 192: 257–261. For evaluating the effects of a test substance on phosphorylation within the normal cellular context, one can also used the rapid and quantitative assays systems described in U.S. Pat. No. 5,763,198. For example, two embodiments may be contemplated as follows.

The extent of phosphorylation of a target protein may be measured by exposing cells that express the target protein to a test substance and, thereafter, lysing the cell to release the cellular contents. The target protein is isolated by incubating the cell lysate with a binding partner to a solid support and thereafter washing away non-bound cellular components. A detection procedure is performed to assess the presence or absence of phosphorylated residues on the protein as compared to lysates of control cells, which were not exposed to the test substance. Alternatively, the binding partner may be directed against the phosphorylated forms of the target protein, so that the steps of isolation and of detection of phosphorylation are performed simultaneously.

These assays offer several advantages. The exposure of the test substance to a whole cell allows for the evaluation of its activity in the natural context in which the test substance may act. In addition, radioactive labeling of the target cell proteins is not required in the assay. Because this assay can readily be performed in a microtitre plate format, the assays described can be performed by an automated robotic system, allowing for testing of large numbers of test samples within a reasonably short time frame.

An alternative embodiment of the invention relates to methods for determining the effect of a test substance on the ability of proteins, such as GADD34L, to dephosphorylate eIF2α in a cell-free system. To assess modulation of enzyme activity, the test substance is added to a reaction mixture containing the phosphatase complex and phosphorylated eIF2α bound to a solid support by an antibody. A detection procedure as described herein is performed on the substance to assess the presence or absence of the phosphorylated residues, and results are compared to those obtained for controls, i.e., reaction mixtures to which the test substance was not added.

The assays of the invention can be used as a screen to assess the activity of a previously untested compound or extract, in which case a single concentration is tested and compared to controls. These assays can also be used to assess the relative potency of a compound by testing a range of concentrations, in a range of 100 μM to 1 pM, for example, and computing the concentration at which the amount of phosphorylation is increased by one-half (IC50) compared to controls.

The whole cell assay of the invention described herein can be performed, for example, by utilizing pre-packaged kits comprising any or all of the reagents of the assay, such as a solid phase coated with a binding partner to a protein of interest, or a detection molecule. The cell-free assays of the invention may be performed, for example, by utilizing pre-packaged kits comprising any or all of the reagents of the assay.

High Throughput Screening Example

CHO K1 cells may be obtained from ATCC and may be cultured in DMEM:F12 in the presence of 10% fetal calf serum (Atlantic Biological). A murine CHOP genomic fragment containing the CHOP promoter may be used. The fragment is 8.5 kb in length, wherein its 3' end corresponds to the PmI site in exon 3, nine nucleotides 5' to the initiation methionine of CHOP. CHO K1 cells may be transfected with expression vectors encoding GADD34L, or portions thereof (such as pCMV2FLAG FL GADD34L, pCMV2FLAG-ΔN GADD34L, or the retroviral clone CD-GSE) and with the CHOP genomic fragment linked to the GFP reporter gene by the Lipofectamine plus method (Gibco-BRL) using 1 μg plasmid DNA per 35 mm plate. Cells may plated 48 hours after transfection to form GADD34L/CHOP-GFP transient reporter cells. Alternatively, the transfection of the reporter plasmid may include 0.1 μg of the Neo$^r$-containing plasmid pcDNA3 (Invitrogen) followed by selection of transfected cells with 0.5 mg/ml of the aminoglycosidic antibiotic G418 (Fisher Scientific) for 10 days to establish stable clones containing the reporter.

GADD34L/CHOP-GFP reporter cells are plated into 96 well microtitre plates at $5 \times 10^3$ cells per well. Individual compounds (test substances) from the DIVERSet™ library, a library of universally diverse, pre-designed 10,000–50,000 drug-like small molecules (ChemBridge Co.), may be tested. The test substances would be added one at a time in an automated fashion at concentrations from $10^{-9}$ M to $10^{-6}$ M to the wells of the microtitre dishes containing the GADD34L/CHOP-GFP reporter cells. Test substances that inhibit GADD34L activity and consequently activate the CHOP gene are identified through fluorescence of the GFP reporter protein using FL600 Microplate Fluorescence and Absorbance Reader (Bio Tek).

Isolation and Characterization of GADD34L

Isolation of GADD34L as a Genetic Suppressor of the Integrated Stress Response

A new regulator of the phospho-eIF2α-dependent Integrated Stress Response (ISR) pathway was identified by screening a library of recombinant retroviruses for clones that inhibit the expression of a CHOP::GFP reporter. A forward somatic cell screen for Genetic Suppressor Elements (GSE) that inhibit ISR target gene expression in cultured Chinese Hamster Ovary (CHO) cells was used. 293T cells were co-transfected with a cDNA library and helper retroviral packaging genes to generate a pseudotyped, replication defective retroviral library that was transduced into a CHO transgenic cell line containing a Green Fluorescent Protein (GFP) reporter controlled by the CHOP promoter (CHOP::GFP cell line).

To form the transgenic cell line, CHO-K1 cells were stably transformed with a CHOP::GFP reporter plasmid. The plasmid was constructed by fusing an 8.5-kb 5' murine CHOP gene fragment, whose 3' end is at the PmII site in exon 3, nine nucleotides 5' of the CHOP coding region, to enhanced green fluorescent protein (GFP) (CLONTECH Laboratories, Inc.) and termination sequences from the SV-40 virus [Wang, X.-Z., Harding, H. P., Zhang, Y., Jolicoeur, E. M., Kuroda, M., and Ron, D. (1998) Cloning of mammalian Ire1 reveals diversity in the ER stress responses. EMBO J. 17:5708–5717]. A clone of CHOP::GFP cells was selected for low basal GFP activity and high inducibility by tunicamycin (Calbiochem-Novabiochem) and amino acid starvation, and was used in all subsequent studies. It is referred to as the parental line.

In wildtype cells, the ER stress-inducing drug tunicamycin activates the endogenous ISR target gene CHOP and its surrogate CHOP::GFP reporter. Cells that have acquired a GSE are predicted to have impaired CHOP::GFP expression. Following retroviral transduction and tunicamycin treatment, cells with reduced CHOP::GFP signal were selected by fluorescence activated cell sorting (FACS). The pool of selected "GFP dull" cells was then transfected with plasmids encoding helper retroviral packaging genes in order to recover a pool of retroviruses enriched in putative GSEs. This enriched pool was transduced into the parental CHOP::GFP cell line and the process of virus rescue and cell sorting was repeated three times. Individual retroviral clones causing decreased CHOP::GFP reporter activity following tunicamycin stress were then analyzed.

Genomic DNA was prepared from these clonal cell lines, and the GSE cDNA inserts were recovered from integrated retroviral clones by PCR using the primers: 5'GAT CCA TGG ATG GAT GGC CAG3' (SEQ ID NO: 5) and 5'GCA TGC TTT GCA TAC TTC TGC CTG3' (SEQ ID NO: 6). Recovered cDNA inserts were ligated into the parental pre-retroviral plasmid, packaged into infectious particles, and transduced into parental CHOP::GFP CHO cells. Reconstitution of the defect in CHOP::GFP expression following tunicamycin treatment was taken as confirmation of the presence of a GSE in the retroviral clone.

This method allowed the isolation of a suppressor of the ISR in a retroviral clone named CD-GSE. The cDNA within this clone was sequenced using vector primers. The partial sequence of the CD-GSE hamster cDNA clone was found to be highly related to several mouse and human sequences deposited in Genbank. These sequences were related, but not identical, to the previously characterized protein GADD34. The protein encoded by the CD-GSE and Genbank clones is therefore hereinafter named GADD34-Like, or GADD34L. The CD-GSE clone cDNA encodes the COOH terminus of GADD34L that includes a domain predicted to bind to the catalytic subunit of PP1c (corresponding to amino acids 314–688 of the mouse protein or 320–705 of the larger human protein).

The full length human GADD34L cDNA (FIG. 2) and translated amino acid (FIG. 3) sequences are available from the National Center for Biotechnology Information (NCBI) website under Genbank Accession Number NM_032833. The full length mouse GADD34L cDNA (FIG. 4) and amino acid (FIG. 5) sequences were deduced following sequencing of IMAGE consortium (LLNL) cDNA clone 961134 (Genbank Accession Number AA547392), 3965646 (Genbank Accession Number BE914017) and 3599662 (Genbank Accession Number BE380181) (all from Research Genetics, Hunstville Ala.) and from the published sequence of the following Genbank accession numbers BI654191, BB527493, BB214542, AA413655, AW910437, BB395632, B1663549, BE648121 and BG695164.

In order to isolate mouse or human GADD34L cDNA fragments suitable for sequencing, subcloning, and use in expression vectors, the desired cDNA fragment can be amplified from an appropriate RNA source using RT-PCR, where the primers are designed based on the provided full length cDNA sequences. For example, an approximately 2 kb mouse GADD34L fragment can be isolated from mouse embryo fibroblast RNA via RT-PCR using the primers G34L.Hind5S (5'TG CCC AAG CTT CGG CGA TCG CAC GCC TGC TC3') (SEQ ID NO: 7) and G34L.Xho6AS (5'GAA ACT CTC GAG TAA GAG ACA GAG TGG GCA CG3') (SEQ ID NO: 8). This cDNA fragment comprises nucleotides 543 through 2603, inclusive, of the full length sequence, and encodes for amino acids 24–698 of the mouse GADD34L protein.

Characterization of GADD34L (a) GADD34L is a Negative Regulator of the ISR

In order to study the function of GADD34L, the retroviral CD-GSE clone was used to drive expression of a partial GADD34L peptide in the parent CHOP::GFP CHO cell line. This expression of exogenous GADD34L from the retroviral clone CD-GSE attenuated CHOP induction and eIF2α phosphorylation in CHO cells following cell stress., indicating that the ISR was suppressed.

In one experiment, parental and CD-GSE-transduced CHOP::GFP CHO cells were treated for 8 hours with 1.75 μg/mL of tunicamycin or 50 μM of arsenite, or left untreated. Expression of the CHOP::GFP transgene was then assessed by FACS analysis to generate quantitative plots of GFP expression. While both tunicamycin and arsenite treatment substantially activated CHOP::GFP reporter expression in the parental CHO cells, neither treatment activated reporter expression in CHO cells expressing a partial GADD34L peptide from the CD-GSE retrovirus.

In a second experiment, parental and CD-GSE-transduced CHOP::GFP CHO cells were treated for varying amounts of time (0, 1, 2, or 4 hours, or 0, 15, 30, 45, or 60 minutes) with 1.75 μg/mL of tunicamycin or 50 μM of arsenite. Western blots of cell lysates were then probed with antisera specific for endogenous CHOP protein and phosphorylated eIF2α. As a protein loading control, the same blots were reacted with an antibody to eIF2α. The antisera for detecting total content of eIF2α and of eIF2α phosphorylated on serine 51 (P-eIF2α) have been described previously [Scorsone, K. A., Panniers, R., Rowlands, A. G., and Henshaw, E. C. (1987). Phosphorylation of eukaryotic initiation factor 2 during physiological stresses which affect protein synthesis. J. Biol. Chem 262:14538–14543; and DeGracia, D. J., Sullivan, J. M., Neumar, R. W., Alousi, S. S., Hikade, K. R., Pittman, J. E., White, B. C., Rafols, J. A., and Krause, G. S. (1997). Effect of brain ischemia and reperfusion on the localization of phosphorylated eukaryotic initiation factor 2 alpha. J. Cereb. Blood Flow Metab 17:1291–1302]. CHOP protein was detected by immunoblot as described previously [Wang, X.-Z., Lawson, B., Brewer, J., Zinszner, H., Sanjay, A., Mi, L., Boorstein, R., Kreibich, G., Hendershot, L., and Ron, D. (1996). Signals from the stressed endoplasmic reticulum induce C/EBP homologous protein (CHOP/GADD153). Mol. Cell. Biol. 16:4273–4280].

The control parental CHO cells showed strong induction of CHOP protein, and an increase in phosphorylated eIF2α levels, following tunicamycin or arsenite treatment. Conversely, GADD34L-expressing CHO cells failed to upregulate CHOP protein levels following tunicamycin or arsenite treatment. Similarly, GADD34L-expressing CHO cells showed severely decreased levels of P-eIF2α (despite strong expression of eIF2α) prior to tunicamycin or arsenite treatment, and furthermore failed to phosphorylate eIF2α following tunicamycin or arsenite treatment.

(b) GADD34L is Part of an eIF2α-Specific PP1c Holophosphatase

The sequence similarity between GADD34L and GADD34 suggested that, like GADD34, GADD34L may function as a regulator of PP1c phosphatase. To test this hypothesis, the effect of GADD34L overexpression on the dephosphorylation of eIF2α, and the ability of GADD34L to associate with PP1 c in vivo, was examined.

A first experiment revealed that cells overexpressing GADD34L have increased phosphatase activity directed toward eIF2α. In this assay, eIF2α from rabbit reticulocyte lysates was radiolabeled in vitro on serine 52 with purified PERK kinase and γ-$^{32}$P-ATP as described previously [Harding, H., Zhang, Y., and Ron, D. (1999). Translation and protein folding are coupled by an endoplasmic reticulum resident kinase. Nature 397:271–274, and]. Radiolabeled P-eIF2α was then incubated in a dephosphorylation reaction as described in [Novoa, I.; Zeng, H., Harding, H., and Ron, D. (2001). Feedback inhibition of the unfolded protein response by GADD34-mediated dephosphorylation of eIF2α. J. Cell Biol., 153, 1011–1022] for 30 min with lysates from CHO cells overexpressing or not overexpressing a partial GADD34L peptide from the CD-GSE retroviral clone. Levels of $^{32}$P-eIF2α were then detected by autoradiography. While exposure to parental CHO cell lysate failed to cause substantial dephosphorylation of eIF2α, exposure to CHO lysate containing exogenous GADD34L resulted in near-complete dephosphorylation of eIF2α.

Another experiment showed that GADD34L and PP1c form a protein complex in vivo. For this assay, pCMV2Flag vector GADD34L expression constructs were transfected into 293T cells. The expression vector pCMV2FLAG FL GADD34L, containing the cDNA sequence encoding mouse GADD34L amino acids 24–698, was constructed by digesting the 2 kb GADD34L RT-PCR product with HindIII and XhoI and ligating the fragment into HindIII and SalI digested pCMV2-Flag vector. The expression vector pCMV2FLAG-ΔN GADD34L, containing the cDNA sequence encoding mouse GADD34L amino acids 418–698, was constructed by ligating the NarI and XbaI fragment of IMAGE consortium clone 9611134 (Genbank Accession Number AA547392, corresponding to nucleotides 1711–2662 of the mouse GADD34 cDNA sequence in FIG. 4A) into AccI and XbaI digested pCMV2-Flag vector. These expression vectors direct the expression of FLAG epitope tagged GADD43L fusion proteins in transfected cells.

Cultured transfected cells were lysed and the immune complex containing GADD34L was isolated by immunoprecipitation using the anti-FLAG antibody (Kodak, IBI). These immunoprecipitates were then immunoblotted. Recombinant GADD34L proteins on the immunoblot were detected with the anti-FLAG antibody, and co-immunoprecipitating endogenous PP1c detected with a rabbit anti-human PP1c antiserum (Santa Cruz Biotechnology, Inc.) at a dilution of 1:200.

PP1c protein was present in anti-FLAG immunoprecipitates containing FLAG-tagged FL GADD34L, and in those containing FLAG-tagged ΔN GADD34L, demonstrating that GADD34L forms a protein complex with PP1c in vivo. The ability of FLAG-ΔN GADD34L to associate with PP1c indicates that the domain responsible for this interaction is located in the C-terminal domain of the GADD34L protein, as predicted. Note that the transfected 293T cells were not subjected to stress prior to lysate immunoprecipitation. Thus, GADD34L association with PP1c is not dependent upon activation of the ISR.

(c) GADD34L is Expressed Constitutively in Cells Not Subject to Stress and is Not Regulated by Stress Further experimentation showed that GADD34L is expressed constitutively in cells not subject to stress and is not regulated by stress. Antiserum to mouse GADD34L can be raised by immunizing a rabbit with 5 injections of 0.3 mg of bacterially expressed mouse GADD34L, where partial GADD34L peptides are expressed as fusion proteins from the pRSET A Vector (Invitrogen) or GST-fusions from the pGEX-2T vector™ (Pharmacia) in bacterial host cells. Thereafter, endogenous GADD34L protein was detected on Western blots of lysates of HT22 cells treated with tunicamycin (2 µg/ml) and arsenite (50 µM) for various time periods (0, 1, 2, or 4 hours).

GADD34 protein is present at low levels in cells not subject to stress, and its expression is dramatically upregulated following cell stress. Conversely, GADD34L was found constitutively in cells not subject to stress and its expression is not upregulated following cell stress. Given that endogenous GADD34L is constitutively expressed, and that association of GADD34L with PP1c is not dependent on activation of the IRS, it follows that the GADD34L:PP1c eIF2α holophosphatase is present constitutively in cells not subject to stress.

Inhibition of GADD34L Activates the ISR in Cells not Subject to Stress

Figure 7:
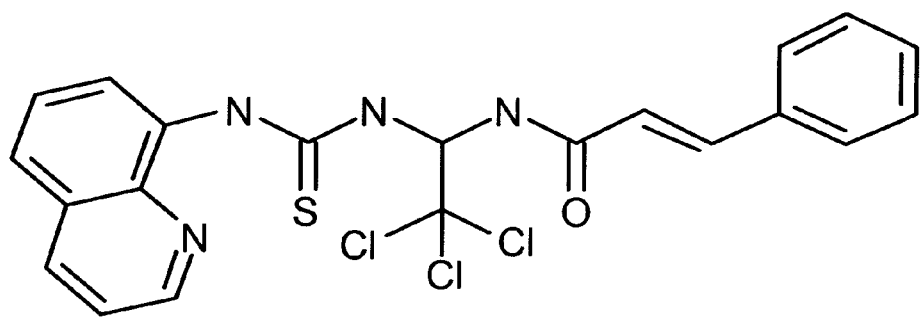
FIG. 7: The structure of 22P19. The chemical compound called 22P19 was isolated by screening the Chembridge™ library (Chembridge San Diego, Calif.) for compounds that protect PC-12 cells from death induced by prolonged exposure to tunicamycin.

The GADD34L:PP1c eIF2α holophosphatase complex may act to repress basal levels of eIF2α phosphorylation. Consequently, inhibition of GADD34L activity that abrogates function of the holophosphatase complex in cells not subject to stress may cause the build-up of phosphorylated eIF2α and activate the ISR. To test this hypothesis, GADD34L activity was inhibited by two independent methods, using GADD34L mRNA directed RNA-interference (RNAi) and using the chemical compound 22P19 (see FIG. 7). The methods described in these tests may be used in methods of screening to identify test substances which inhibit GADD34L.

RNAi-Based Inhibition of Endogenous GADD34L Activates the ISR in Cells not Subject to Stress The RNAi technique is based on the use of sequence-specific double stranded (complementary sense:antisense duplex) RNA to stimulate the degradation of target endogenous sense RNAs containing the same sequence. GADD34L mRNA targeted RNAi was used to inhibit the production of endogenous GADD34L in the parental CHOP::GFP CHO cell line. This inhibition activates the ISR as assayed by expression of the CHOP::GFP reporter.

Complementary double stranded RNA oligonucleotides of the sequence 5'-GGG AUG GAU GCA GGU UCC AdTdT-3' (SEQ ID NO: 9) and 5'-U GGA ACC UGC AUC CAU CCC dTdT-3' (SEQ ID NO: 10) were purchased from Dharmacon Inc. The oligonucleotides arrived in an annealed and desalted form from the manufacturer and were used to transfect CHO CHOP::GFP cells using Oligofectamine™ (Invitrogen, Life Science Inc). Briefly CHO cells were plated at 14000 cells per well of a 24-wells dish, grown overnight and transfected with 2.5 µL of 20 µM siRNA duplex using 1.5 µL Oligofectamine in a total volume of 250 µL of medium.

Cells were harvested 16, 24, or 44 hours after transfection. Expression of the CHOP::GFP transgene in these cells not subject to stress was then assessed quantitatively using by FACS analysis. By this method it was determined that inhibition of GADD34L using the siRNA duplex activates CHOP::GFP expression in cells not subject to stress.

Chemical Compound 22P19 Inhibits the eIF2α Phosphatase Activity of GADD34L and Activates the ISR in Cell Not Subject to Stress The chemical compound called 22P19 (see FIG. 7) was isolated by screening the Chembridge™ library (Chembridge San Diego, Calif.) for compounds that protect PC-12 cells from death induced by prolonged exposure to tunicamycin. Treatment of cells not subject to stress with 22P19 inhibits GADD34L phosphatase activity and activates the ISR.

The first experiment revealed that 22P19 inhibits the eIF2α phosphatase activity of cells overexpressing GADD34L. In this assay, eIF2α from rabbit reticulocyte lysates was radiolabeled in vitro on serine 52 with purified PERK kinase and $\gamma$-$^{32}$P-ATP as described previously [Harding, H., Zhang, Y., and Ron, D. (1999). Translation and protein folding are coupled by an endoplasmic reticulum resident kinase. Nature 397:271–274, and]. Radiolabeled P-eIF2α was then incubated for 0, 10, or 20 minutes in a dephosphorylation reaction with cell lysates [as described in Novoa, I.; Zeng, H., Harding, H., and Ron, D. (2001). Feedback inhibition of the unfolded protein response by GADD34-mediated dephosphorylation of eIF2α. J. Cell Biol., 153, 1011–1022]. Cell lysates were from parental CHOP::GFP CHO cells and CD-GSE transformed CHOP::GFP CHO cells expressing exogenous GADD34L that were left untreated for 24 hours, treated with DMSO carrier for 24 hours, or treated with 70 µM 22P19 in DMSO for 4 or 24 hours prior to lysate preparation. Levels of $^{32}$P-eIF2α were then detected by autoradiography. As expected, lysates from control GADD34L-expressing cells were able to substantially dephosphorylate eIF2α in a 20 minute dephosphorylation reaction (22 $^{32}$P counts versus 100 input for untreated, and 13 $^{32}$P counts versus 98 input for DMSO treated) Conversely, lysates from GADD34L-expressing cells that had been pretreated with 22P19 for 24 hours failed to substantially dephosphorylate eIF2α in a 20 minute dephosphorylation reaction (60 $^{32}$P counts versus 99 input), similar to lysates from untreated parental cells not expressing exogenous GADD34L (65 $^{32}$P counts versus 91 input). This result indicated that prolonged 22P19 exposure inhibited the phosphatase action of the exogenous GADD34L.

A second experiment showed that treatment with the GADD34L-inhibitor 22P19 activates the IRS in cells not subject to stress. In this assay, HT22 cells were treated with 70 µM 22P19 for varying amounts of time (1, 4, 8, 16, 24, or 32 hours). Western blots of cell lysates were then probed with antisera specific for endogenous phosphorylated eIF2α (P-eIF2α), eIF2α, CHOP, and GADD34 proteins. Control untreated HT22 cells showed low levels of P-eIF2α, despite strong eIF2α expression, contained no CHOP protein, and expressed very low levels of GADD34 protein. This protein profile represents the basal state of cells not subjected to stress. HT22 cells treated with 22P19 for 4 hours or more activated phosphorylation of eIF2α to generate P-eIF2α and activated expression of both CHOP and GADD34 proteins. This protein profile indicated that the ISR was activated in HT22 cells not subjected to stress by 22P19 treatment. Note that eIF2α phosphorylation and induction of ISR target genes was sustained in 22P19-treated cells for up to 32 hours. In cells subject to stress, eIF2α phosphorylation is typically transient, due to the induction of GADD34 which dephosphorylates eIF2α. But as 22P19 also inhibits GADD34 phosphatase activity, this rectifying response did not occur in 22P19-treated cells.

Preconditioning Induced by Inhibition of GADD34L Protects Cells against Oxidative Toxicity The described experiments demonstrated that inhibition of GADD43L promotes an ISR in cells not subject to stress. In order to determine whether this preconditioning is protective against subsequent cell stress, cell survival rates of HT22 cells following toxic glutamate exposure were measured, where those HT22 cells had been preconditioned by 22P19- or RNAi-mediated inhibition of GADD34L (see FIG. 6).

Figure 6:
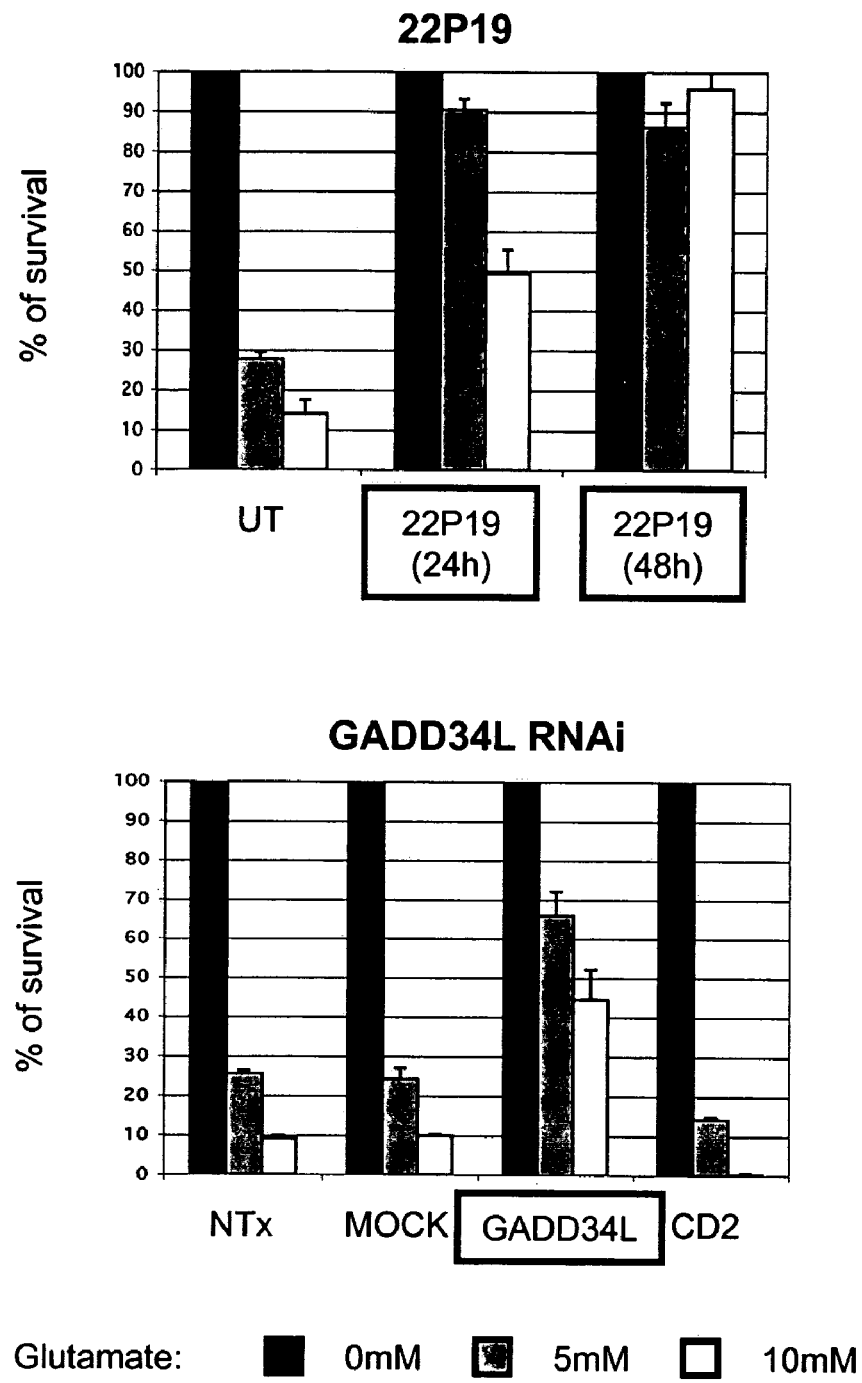
FIG. 6: Inhibition of endogenous GADD34L protects cells against oxidative toxicity. The bar graphs show percent survival of HT22 cells following exposure to toxic amounts of glutamate. HT22 cells were treated with 70 μM 22P19 for 24 or 48 h (top panel), or left untransfected (NTx), mock transfected, transfected with GADD34L siRNA, or transfected with control or CD2 siRNA (bottom panel), and then exposed to the indicated concentrations of glutamate for 18 hours. 100% survival is defined as the level of MTT ((3-[4, 5-dimethylthiazol-2-yl]-2,5-diphenyl tetrazolium bromide, Sigma) cleavage in cells that had not been exposed to glutamate in each treatment group. Shown are the means±SEM of a representative experiment performed in duplicate and repeated four times. There was dramatically improved cell survival following pre-treatment with 22P19, or RNAi-based inhibition of GADD34L. 22P19 is a chemical inhibitor of GADD34L isolated in a high-throughput screen based on its ability to protect cells from tunicamycin toxicity.

For this assay, HT22 cells were either treated with 70 μM 22P19 for 24 or 48 h, or transfected with GADD34L siRNA or control CD2 siRNA, and then exposed to 0 mM, 5 mM, or 10 mM glutamate for 18 hours. Percent cell survival for each group was then calculated where 100% survival was defined as the MTT ((3-[4,5-dimethylthiazol-2-yl]-2,5-diphenyl tetrazolium bromide, Sigma) cleavage reduction in cells that had not been exposed to glutamate in each treatment group. Final cell survival calculations represented the means±SEM of a representative experiment performed in duplicate and repeated four times. Percent survival of 22P19 and GADD34L siRNA preconditioned cells was then compared to that of non-preconditioned cells (FIG. 6). Preconditioning with either 22P19 or GADD34L siRNA substantially improved cell survival following glutamate treatment, indicating that inhibition of GADD34L protects cells against oxidative stress.

This invention is thus directed to a method for screening a plurality of test substances useful for the prevention or treatment of a disease involving an oxidative stress, which comprises the steps of i) testing each of the test substances for its ability to inhibit the activity of GADD34L and ii) identifying the test substance which inhibits the activity of GADD34L, thereby to identify a test substance useful as a preventive or therapeutic agent for a disease involving an oxidative stress. This invention is further directed to a method for identifying a test substance useful for the prevention or treatment of a disease involving an oxidative stress, which comprises testing a test substance for its ability to inhibit the activity of GADD34L, thereby to determine whether the substance promotes resistance to cell stress, and to identify said substance as a preventive or therapeutic agent for a disease involving an oxidative stress. In one embodiment, the test substance inhibits GADD34L activity by disrupting the formation of the GADD34L and PP1c protein complex. In another embodiment, the test substance inhibits the production of GADD34L protein from the GADD34L mRNA. In another embodiment, the test substance inhibits the production of GADD34L mRNA from the GADD34L genomic locus. In another embodiment, the method further comprises a step of verifying whether said test substance does not cause stress to cells.

The invention is directed to a method, which comprises the steps of i) contacting the test substance or each of the test substances with a cell-free composition containing GADD34L and PP1c proteins in the form of a purified complex and eIF2α in a phosphorylated form, ii) assessing the level of phosphorylation of eIF2α, in comparison with the level of phosphorylation determined in the absence of test substances, in a cell-free composition containing GADD34L and PP1c proteins in the form of a purified complex and eIF2α in a phosphorylated form, and iii) identifying the test substance which provides a higher level of phosphorylation of eIF2α, in comparison with the level of phosphorylation determined in the absence of test substance, thereby to identify a test substance useful as a preventive or therapeutic agent for a disease involving an oxidative stress. In one embodiment, the assessment of the level of phosphorylation of eIF2α is effected by an immunoassay using an antibody that specifically recognizes the phosphorylated form of eIF2α. In another embodiment, the assessment of the level of phosphorylation of eIF2α is effected by tracking the covalent binding of a radiolabelled phosphate group to eIF2α.

The invention is directed to a method, which comprises the steps of i) contacting a test substance or each of the test substances with cells not subject to stress that contain PP1c and eIF2α and overexpress GADD34L, or portions thereof, ii) assessing the level of phosphorylation of eIF2α after contact with the test substance or test substances, in comparison with the level of eIF2α phosphorylation in the absence of test substances, and iii) identifying the test substance which provides a higher level of phosphorylation of eIF2α, in comparison with the level of phosphorylation determined in the absence of test substance, thereby to identify a test substance useful as a preventive or therapeutic agent for a disease involving an oxidative stress. In one embodiment, the assessment of the level of phosphorylation of eIF2α is effected by an immunoassay using an antibody that specifically recognizes the phosphorylated form of eIF2α. In another embodiment, the assessment of the level of phosphorylation of eIF2α is effected by tracking the covalent binding of a radiolabelled phosphate group to eIF2α. In an additional embodiment, the assessment of the level of phosphorylation of eIF2α is conducted additionally on exogenous radiolabeled eIF2α following either in vivo or in vitro exposure to cell lysates, where such assessment can provide more detailed information concerning the affect of test substances on the rate and enzyme kinetics of the eIF2α-specific phosphatase.

The invention is directed to a method, which comprises the steps of i) contacting a test substance or each of the test substances with cells that normally express endogenous GADD34L, ii) and identifying a test substance that inhibits the expression of endogenous GADD34L, thereby to identify a test substance useful as a preventive or therapeutic agent for a disease involving an oxidative stress. In one embodiment, the level of GADD34L expression is assessed by determining the level of transcription of GADD34L. In a further embodiment, determination of the level of transcription of GADD34L is effected by means of a Northern blot. In a further embodiment determination of the level of transcription of GADD34L is effected by means of in situ hybridization. In another embodiment, the level of GADD34L expression is assessed by the level of translation of GADD34L. In a further embodiment, determination of the level of translation of GADD34L is effected by means of an immunoassay.

The invention is directed to a method, which comprises the steps of i) contacting a test substance or each of the test substances with cells not subject to stress that overexpress GADD34L, or portions thereof, ii) assessing the expression of a target gene, and iii) identifying a test substance that activates the expression of the target gene, thereby to identify a test substance useful as a preventive or therapeutic agent for a disease involving an oxidative stress. In one embodiment, the target gene is the CHOP gene.

The invention is directed to a method, which comprises the steps of i) obtaining cells not subject to stress that overexpress GADD34L, or portions thereof, and have been transfected with a reporter gene operatively associated with all or part of the promoter of a target gene, and ii) contacting a test substance or each of the test substances with these cells, and assaying the level of expression of said reporter gene, and iii) identifying a test substance that activates the expression of the reporter gene, thereby to identify a test substance useful as a preventive or therapeutic agent for a disease involving an oxidative stress. In one embodiment, the target gene is the CHOP gene. In another embodiment, said reporter gene encodes one of the group consisting of GFP, CAT, GAL, LUC, and GUS.

The invention is directed to a method, which comprises the steps of i) obtaining cells not subject to stress which overexpress GADD34L, or portions thereof, ii) contacting a test substance or each of the test substances with the cells, in the presence of a toxic agent that induces oxidative stress, iii) quantitating cell survival of cells that overexpress GADD34L, or portions of GADD34L, following exposure to the toxic agent in the presence and absence of test substances, iv) and identifying a test substance that promotes cell survival of the cells following exposure to concentrations of toxic agent that induce oxidative stress, thereby to identify a test substance useful as a preventive or therapeutic agent for a disease involving an oxidative stress. In one embodiment, the toxic agent which induces oxidative stress is tunicamycin, arsenite, or glutamate.

In one embodiment, the identified test substance is useful for the prevention or treatment of a disease involving neuronal ischemia. In a further embodiment, the identified test substance is useful for the prevention or treatment of a disease involving heart ischemia. In another embodiment, the identified test substance is useful for the prevention or treatment of renal damage induced by ischemia or toxins. In another embodiment, the identified test substance is useful for the prevention or treatment of an auto-immune disease. In a further embodiment, the selected compound is useful for the prevention or treatment of a neurodegenerative disorder.

The invention is directed to a method for the prevention or treatment of a disease involving an oxidative stress in a patient in need of such treatment, which comprises administering to the patient an effective amount of a GADD34L inhibitor identified for its ability to promote resistance to cell stress while not causing stress. In one embodiment, the disease is a disease involving neuronal ischemia, a disease involving heart ischemia, a disease involving renal damage induced by ischemia or toxins, an auto-immune disease, or a neurodegenerative disorder.

The invention is also directed to a pharmaceutical composition, comprising a therapeutic agent identified as being capable of promoting resistance to cell stress while not causing stress, in association with a pharmaceutically acceptable carrier. This therapeutic agent is defined as a substance that can activate the expression of a target gene of the Integrated Stress Response pathway, while not being toxic, which means more particularly that it does not cause stress to the cell. These properties may be determined by the methods of screening as above described.

Therapeutic agents that promote preconditioning and may be developed by this platform technology may more particularly prevent cognitive and neurological dysfunction in patients undergoing cardiopulmonary bypass, if administered prophylactically or during the procedure. They may also protect the myocardium, kidneys and intestine from damage incurred during cardio-pulmonary bypass. Such therapeutic agents may also be efficacious in circumstances where neurological damage by ROS may be anticipated, such as early in the course of head trauma, in the post-neurosurgery period, following surgical procedures for brain re-vascularization, or in the treatment of status epilepticus.

The therapeutic agents may be administered locally to preserve function of specific organs that are to be subjected to ischemic stress. For example, intracoronary instillation to preserve myocardial function in preparation of cardiac surgery, or injection into the renal artery to preserve kidney function in preparation for surgery on the abdominal aorta. Therapeutic agents developed by this platform technology may be used ex-vivo in the preservation of organs and cells procured for purpose of transplantation from live or cadaver donors. For example, the essential role of PERK in promoting survival of pancreatic islets of Langerhans suggests that activating the ISR will promote survival of such cells ex-vivo and extend their utility in transplantation therapy of Diabetes Mellitus.

This platform technology may also be useful for identifying lead compounds for drug development to treat chronic diseases associated with cell and tissue damage caused by ROS. Examples of such conditions include Diabetes Mellitus, Parkinson's Disease and Cirrhosis.

What is claimed is:

1. A method for screening a plurality of test substances useful as a preventive or therapeutic agent for a disease involving an oxidative stress, which comprises the steps of
   i) testing each of the test substances to determine if it inhibits an activity of a GADD34L protein and
   ii) identifying the test substance which inhibits the activity of said GADD34L protein, and selecting as a test substance useful as a preventive or therapeutic agent for a disease involving an oxidative stress each test substance that inhibits the activity of said GADD34L protein.

2. A method for identifying a test substance useful as a preventive or therapeutic agent for a disease involving an oxidative stress, which comprises testing a test substance to determine if it inhibits an activity of a GADD34L protein, thereby to determine whether the test substance promotes resistance to oxidative cell stress, and to identify said test substance as a preventive or therapeutic agent for a disease involving an oxidative stress.

3. The method according to claim 1 or 2, wherein the test substance inhibits an activity of a GADD34L protein by disrupting formation of a protein complex by the GADD34L protein and a PP1 c protein.

4. The method according to claim 1 or 2, wherein the test substance inhibits an activity of a GADD34L protein by inhibiting production of the GADD34L protein from a GADD34L mRNA.

5. The method according to claim 1 or 2, wherein the test substance inhibits an activity of a GADD34L protein by inhibiting production of a GADD34L mRNA from a GADD34L genomic locus.

6. The method according to claim 2, further comprising a step of verifying whether said test substance does not cause stress to cells.

7. The method according to claim 1 or 2, which comprises the steps of
   i) contacting a test substance or each of the test substances with a cell-free composition comprising a GADD34L protein and a PP1 c protein in the form of a purified complex and an eIF2α protein in a phosphorylated form,
   ii) assessing a level of phosphorylation of the eIF2α protein in comparison with the level of phosphorylation of the eIF2α protein determined in the absence of the test substance or each of the test substances, in a cell-free composition comprising a GADD34L protein and a PP1c protein in the form of a purified complex and an eIF2α protein in a phosphorylated form, and
   iii) identifying the test substance which provides a higher level of phosphorylation of the eIF2α protein, in comparison with the level of phosphorylation of the eIF2α protein determined in the absence of the test substance or each of the test substances, thereby to identify a test substance useful as a preventive or therapeutic agent for a disease involving an oxidative stress.

8. The method according to claim 7, wherein assessing a level of phosphorylation of the eIF2α protein is effected by an immunoassay using an antibody that specifically recognizes a phosphorylated form of the eIF2α protein.

9. The method according to claim 7, wherein assessing a level of phosphorylation of the eIF2α protein is effected by assessing covalent binding of a radiolabelled phosphate group to the eIF2α protein.

10. The method according to claim 1 or 2, which comprises the steps of
    i) contacting a test substance or each of the test substances with a cell not subject to stress that comprises a PP1c protein and an eIF2α protein and that overexpresses a GADD34L protein, or a portion thereof,
    ii) assessing a level of phosphorylation of the eIF2α protein after contact with the test substance or each of the test substances, in comparison with a level of phosphorylation of the eIF2α protein in the absence of the test substance or each of the test substances, and
    iii) identifying the test substance which provides a higher level of phosphorylation of the eIF2α protein, in comparison with a level of phosphorylation of the eIF2α protein determined in the absence of test substance, thereby to identify a test substance useful as a preventive or therapeutic agent for a disease involving an oxidative stress.

11. The method according to claim 10, wherein assessing a level of phosphorylation of the eIF2α protein is effected by an immunoassay using an antibody that specifically recognizes a phosphorylated form of the eIF2α protein.

12. The method according to claim 10, wherein assessing a level of phosphorylation of the eIF2α protein is effected by assessing covalent binding of a radiolabelled phosphate group to the eIF2α protein.

13. The method according to claim 1 or 2, which comprises the steps of,
    i) contacting a test substance or each of the test substances with a cell that expresses an endogenous GADD34L,
    ii) and identifying a test substance that inhibits the expression of the endogenous GADD34L, thereby to identify a test substance useful as a preventive or therapeutic agent for a disease involving an oxidative stress.

14. The method according to claim 13, wherein a level of expression of the endogenous GADD34L is assessed by determining a level of transcription of the endogenous GADD34L.

15. The method according to claim 14, wherein determining a level of transcription of the endogenous GADD34L is effected by means of a Northern blot.

16. The method according to claim 14, wherein determining a level of transcription of the endogenous GADD34L is effected by means of in situ hybridization.

17. The method according to claim 13, wherein a level of expression of the endogenous GADD34L is assessed by determining a level of translation of the endogenous GADD34L.

18. The method according to claim 17, wherein determining a level of translation of the endogenous GADD34L is effected by means of an immunoassay.

19. The method according to claim 1 or 2, which comprises the steps of
   i) contacting a test substance or each of the test substances with a cell not subject to stress that overexpresses a GADD34L protein, or a portion thereof,
   ii) assessing an expression level of a target gene, and
   iii) identifying a test substance that increases the expression level of the target gene, thereby to identify a test substance useful as a preventive or therapeutic agent for a disease involving an oxidative stress.

20. The method according to claim 19, where the target gene is a CHOP gene.

21. The method according to claim 1 or 2, which comprises the steps of,
   i) providing a cell not subject to stress that overexpresses a GADD34L protein, or a portion thereof, and which comprises a reporter gene operatively associated with all or part of a promoter of a target gene,
   ii) contacting a test substance or each of the test substances with the cell, and assaying a level of expression of said reporter gene, and
   iii) identifying a test substance that increases the expression level of the reporter gene, thereby to identify a test substance useful as a preventive or therapeutic agent for a disease involving an oxidative stress.

22. The method according to claim 21, where the target gene is a CHOP gene.

23. The method according to claim 21, wherein said reporter gene is selected from the group consisting of GFP, CAT, GAL, LUC, and GUS.

24. The method according to claim 1 or 2, which comprises the steps of,
   i) providing a cell not subject to stress that overexpresses a GADD34L protein, or a portion thereof,
   ii) contacting a test substance or each of the test substances with the cell, in the presence of a toxic agent that induces oxidative stress,
   iii) quantitating cell survival of the cell following exposure to the toxic agent in the presence and absence of the test substance or each of the test substances, and
   iv) identifying a test substance that promotes cell survival of the cell following exposure to a concentration of the toxic agent that induces oxidative stress, thereby to identify a test substance useful as a preventive or therapeutic agent for a disease involving an oxidative stress.

25. The method according to claim 24 wherein the toxic agent that induces oxidative stress is tunicamycin, arsenite, or glutamate.

26. The method according to claim 1 or 2, wherein the disease involving an oxidative stress is neuronal ischemia.

27. The method according to claim 1 or 2, wherein the disease involving an oxidative stress is heart ischemia.

28. The method according to claim 1 or 2, wherein the disease involving an oxidative stress is renal damage induced by ischemia or toxins.

29. The method according to claim 1 or 2, wherein the disease involving an oxidative stress is an autoimmune disease.

30. The method according to claim 1 or 2, wherein the disease involving an oxidative stress is a neurodegenerative disorder.

31. The method according to claim 1, further comprising a step of verifying whether said test substance does not cause stress to cells.

* * * * *

SEQUENCE LISTING

```
<160> NUMBER OF SEQ ID NOS: 10

<210> SEQ ID NO 1
<211> LENGTH: 2942
<212> TYPE: DNA
<213> ORGANISM: Homo sapiens

<400> SEQUENCE: 1
attttgggct tcgcttccac cgcaccagcc ggcctaccca gtccttccgg tatcgcgttg      60
ctcaggggct tttcaaccct ctgtcagtcg gaaaaccatc gccgaggccg tgggggact     120 cctatccatg gtgttgaagc gtcgagccga ctagggaacc tccttcccg ccaggatgga     180 agtcgcatca gtcgccgcct attgcgcggg ctgttcttcc ctgtgttctg ccgcccgctg    240
```

```
ccgcattcgc tgccctctgt ggcttttctg ctggctcgaa gatcggcctg gagcagcgac    300
gccaccgctg ggcaaggccg agactctgta ggcttcctcc gaatcccgtc gacctccagc    360
cgctgagcgc cgcggcccta cctgagagac tgtcaagaaa aaggagatgg agccggggac    420
aggcggatcg cggaaacggc ttggccctcg ggcgggcttc cggttctggc cacccttttt    480
ccctcggcga tcgcaagcag gctcttctaa gttcccgacg cctcttggcc cggaaaactc    540
cgggaacccc acactgcttt cctctgccca gcccgagact cgggtcagtt actggacgaa    600
actgctctcc cagctccttg cgccgctccc cggattgctt cagaaggtgc taatttggag    660 ccaactttc ggtggaatgt ttccgaccag atggctagat tttgctggag tctacagcgc    720
cctgagagcc ctgaagggac gggagaaacc agccgccccc acagcgcaga atctttgag    780 ttcgctgcag ctcgactcct cagacccctc ggtcaccagt ccccttgatt ggctagagga    840
ggggatccac tggcaatact cgcccccaga cctaaaattg gagcttaagg ccaagggaag    900
tgctttggac cctgcagcac aggcttttct cttagcagcag cagctgtggg gagtggagct    960
gttgcccagt agccttcaat cccgtctgta ctctaaccgg gaacttggct cttcgccctc   1020
tgggcctcta acattcaac gcatagacaa tttcagtgtg gtatcctatt tgctgaaccc    1080
ttcctacctg gactgctttc ctaggctaga agtcagctat cagaacagtg atggaaatag   1140
cgaggtagtc ggcttccaga cactaacccc agagagcagc tgcctgagag aggaccattg   1200
tcatccccag ccgctgagtg cagaactcat tccggcctcg tggcagggat gtccacctct   1260
ttctacggaa ggcctaccag aaattccaca tcttcgcatg aaacggctgg aattccttca   1320
acaggctaac aaggggcaag atttacccac ccctgaccag gataatggct accacagcct   1380
ggaggaggaa cacagccttc tccggatgga tccaaaacac tgcagagata cccaacaca    1440 gtttgttcct gctgctggag acattcctgg aaacacccag gaatccactg aagaaaaaat   1500
agaattatta actacagagg ttccacttgc tttggaagaa gagagccctt ctgagggctg   1560
tccatctagt gagataccta tggaaaagga gcctggagag ggccgaataa gtgtagttga   1620
ttactcatac ctagaaggtg accttcccat ttctgccaga ccagcttgta gtaacaaact   1680
gatagattat attttgggag gtgcatccag tgacctggaa acaagttctg atccagaagg   1740
tgaggattgg gatgaggaag ctgaggatga tggttttgat agtgatagct cactgtcaga   1800
ctcagacctt gaacaagacc ctgaagggct tcacctttgg aactctttct gcagtgtaga   1860
tccttataat ccccagaact ttacagcaac aattcagact gctgccagaa ttgttcctga   1920
agagccttct gattcagaga aggatttgtc tggcaagtct gatctagaga attcctccca   1980
gtctggaagc cttcctgaga cccctgagca tagttctggg gaggaagatg actgggaatc   2040
tagtgcagat gaagcagaga gtctcaaact gtggaactca ttctgtaatt ctgatgaccc   2100
ctacaaccct ttaaattta aggctccttt tcaaacatca ggggaaaatg agaaaggctg    2160
tcgtgactca aagaccccat ctgagtccat tgtggccatt tctgagtgtc acccttact    2220 ttcttgtaag gtgcagctgt ggggagcca agaaagtgaa tgtccagact cggtacagcg    2280
tgacgttctt tctggaggaa gacacacaca tgtcaaaaga aaaaggtaa ccttccttga    2340 agaagttact gagtattata taagtggtga tgaggatcgc aaaggaccat gggaagaatt    2400
tgcaagggat ggatgcaggt tccagaaacg aattcaagaa acagaagatg ctattggata    2460
ttgcttgaca tttgaacaca gagaaagaat gtttaataga ctccagggaa catgcttcaa    2520
aggacttaat gttctcaagc aatgttgagt tggcagcctg tagtcctagc tagcatacac    2580
tacctcttac ctgagaggtg tctttaaaa acaaatcttg gcagctgtcc tttgacattt    2640
```

```
ttttttttag aggaaatgta acttggatct agtttaattt ttttttttgc aacatatccc   2700
actcagaaac attcaggttt gaagccagcc ctgataatga aggatgaact agtgtgattt   2760
ctaatcctcc cttttttgat ttagttggat gtgcttttaa atgtcctttg cctgcatgag   2820
gtggaaaggg gaccttttg agttgtcatt ttgcactttc aaaacttatt ttcttggaaa   2880
acaatattta tagggcttaa agcccatttt catttctaat ctaaattatg tgtgcctatc   2940
tg                                                                  2942
```

<210> SEQ ID NO 2
<211> LENGTH: 713
<212> TYPE: PRT
<213> ORGANISM: Homo sapiens

<400> SEQUENCE: 2

```
Met Glu Pro Gly Thr Gly Gly Ser Arg Lys Arg Leu Gly Pro Arg Ala
1               5                   10                  15

Gly Phe Arg Phe Trp Pro Pro Phe Phe Pro Arg Arg Ser Gln Ala Gly
            20                  25                  30

Ser Ser Lys Phe Pro Thr Pro Leu Gly Pro Glu Asn Ser Gly Asn Pro
        35                  40                  45

Thr Leu Leu Ser Ser Ala Gln Pro Glu Thr Arg Val Ser Tyr Trp Thr
    50                  55                  60

Lys Leu Leu Ser Gln Leu Leu Ala Pro Leu Pro Gly Leu Leu Gln Lys
65                  70                  75                  80

Val Leu Ile Trp Ser Gln Leu Phe Gly Gly Met Phe Pro Thr Arg Trp
                85                  90                  95

Leu Asp Phe Ala Gly Val Tyr Ser Ala Leu Arg Ala Leu Lys Gly Arg
            100                 105                 110

Glu Lys Pro Ala Ala Pro Thr Ala Gln Lys Ser Leu Ser Ser Leu Gln
        115                 120                 125

Leu Asp Ser Ser Asp Pro Ser Val Thr Ser Pro Leu Asp Trp Leu Glu
    130                 135                 140

Glu Gly Ile His Trp Gln Tyr Ser Pro Pro Asp Leu Lys Leu Glu Leu
145                 150                 155                 160

Lys Ala Lys Gly Ser Ala Leu Asp Pro Ala Ala Gln Ala Phe Leu Leu
                165                 170                 175

Glu Gln Gln Leu Trp Gly Val Glu Leu Leu Pro Ser Ser Leu Gln Ser
            180                 185                 190

Arg Leu Tyr Ser Asn Arg Glu Leu Gly Ser Ser Pro Ser Gly Pro Leu
        195                 200                 205

Asn Ile Gln Arg Ile Asp Asn Phe Ser Val Val Ser Tyr Leu Leu Asn
    210                 215                 220

Pro Ser Tyr Leu Asp Cys Phe Pro Arg Leu Glu Val Ser Tyr Gln Asn
225                 230                 235                 240

Ser Asp Gly Asn Ser Glu Val Val Gly Phe Gln Thr Leu Thr Pro Glu
                245                 250                 255

Ser Ser Cys Leu Arg Glu Asp His Cys His Pro Gln Pro Leu Ser Ala
            260                 265                 270

Glu Leu Ile Pro Ala Ser Trp Gln Gly Cys Pro Pro Leu Ser Thr Glu
        275                 280                 285

Gly Leu Pro Glu Ile His His Leu Arg Met Lys Arg Leu Glu Phe Leu
    290                 295                 300

Gln Gln Ala Asn Lys Gly Gln Asp Leu Pro Thr Pro Asp Gln Asp Asn
```

```
                      305                 310                 315                 320
             Gly Tyr His Ser Leu Glu Glu His Ser Leu Leu Arg Met Asp Pro
                              325                 330                 335

Lys His Cys Arg Asp Asn Pro Thr Gln Phe Val Pro Ala Ala Gly Asp
                              340                 345                 350

Ile Pro Gly Asn Thr Gln Glu Ser Thr Glu Lys Ile Glu Leu Leu
                              355                 360                 365

Thr Thr Glu Val Pro Leu Ala Leu Glu Glu Glu Ser Pro Ser Glu Gly
                 370                 375                 380

Cys Pro Ser Ser Glu Ile Pro Met Glu Lys Glu Pro Gly Glu Gly Arg
             385                 390                 395                 400

Ile Ser Val Val Asp Tyr Ser Tyr Leu Glu Gly Asp Leu Pro Ile Ser
                              405                 410                 415

Ala Arg Pro Ala Cys Ser Asn Lys Leu Ile Asp Tyr Ile Leu Gly Gly
                              420                 425                 430

Ala Ser Ser Asp Leu Glu Thr Ser Ser Asp Pro Glu Gly Glu Asp Trp
                              435                 440                 445

Asp Glu Glu Ala Glu Asp Asp Gly Phe Asp Ser Asp Ser Ser Leu Ser
                 450                 455                 460

Asp Ser Asp Leu Glu Gln Asp Pro Glu Gly Leu His Leu Trp Asn Ser
             465                 470                 475                 480

Phe Cys Ser Val Asp Pro Tyr Asn Pro Gln Asn Phe Thr Ala Thr Ile
                              485                 490                 495

Gln Thr Ala Ala Arg Ile Val Pro Glu Glu Pro Ser Asp Ser Glu Lys
                              500                 505                 510

Asp Leu Ser Gly Lys Ser Asp Leu Glu Asn Ser Ser Gln Ser Gly Ser
                              515                 520                 525

Leu Pro Glu Thr Pro Glu His Ser Ser Gly Glu Glu Asp Asp Trp Glu
                 530                 535                 540

Ser Ser Ala Asp Glu Ala Glu Ser Leu Lys Leu Trp Asn Ser Phe Cys
             545                 550                 555                 560

Asn Ser Asp Asp Pro Tyr Asn Pro Leu Asn Phe Lys Ala Pro Phe Gln
                              565                 570                 575

Thr Ser Gly Glu Asn Glu Lys Gly Cys Arg Asp Ser Lys Thr Pro Ser
                              580                 585                 590

Glu Ser Ile Val Ala Ile Ser Glu Cys His Thr Leu Leu Ser Cys Lys
                              595                 600                 605

Val Gln Leu Leu Gly Ser Gln Glu Ser Glu Cys Pro Asp Ser Val Gln
                 610                 615                 620

Arg Asp Val Leu Ser Gly Gly Arg His Thr His Val Lys Arg Lys Lys
             625                 630                 635                 640

Val Thr Phe Leu Glu Glu Val Thr Glu Tyr Tyr Ile Ser Gly Asp Glu
                              645                 650                 655

Asp Arg Lys Gly Pro Trp Glu Glu Phe Ala Arg Asp Gly Cys Arg Phe
                              660                 665                 670

Gln Lys Arg Ile Gln Glu Thr Glu Asp Ala Ile Gly Tyr Cys Leu Thr
                              675                 680                 685

Phe Glu His Arg Glu Arg Met Phe Asn Arg Leu Gln Gly Thr Cys Phe
                 690                 695                 700

Lys Gly Leu Asn Val Leu Lys Gln Cys
             705                 710

<210> SEQ ID NO 3
```

-continued

<211> LENGTH: 5468
<212> TYPE: DNA
<213> ORGANISM: Mus musculus

<400> SEQUENCE: 3

```
cggtcctccg tctcgccctg cagcttccgg gtgtgcggct gcggccattt tgagcttcgc      60
ttctttgcgc cctcgcctgc cacccagcca ccctttccgc cttggcgttt cgcgcctccg     120
tgcgggccac cggaaacgcc gccgtcgtct ccgtcgccgc cgcgcgaggg agggtcttct     180
ctatggtgga gcgatctcac acggcctagg acgtctcctt ccctagccgg gatggaccta     240
accgcggtcg ccaccgcttg cgcgggcctc tgggccgtcc ggtgcagcac tcgttgcgga     300
agccgccgct ctctgggcct cctctgccgg cgcgggaatc ggactgcagt acccactccg     360
tggctgggca aggcggagac tgtgtagacc tcggatccag cctgcgctga cgccgctgag     420
ctctgtcctc ctcctgtctg agaagccgcc aaggaaagga gatggagaca ggaacgcaca     480
gggcccggaa gcgcctggc  cctcggctgg gctcctggtt ccggctgccc ttccttcggc     540
gatcgcacgc ctgctcttcg gagttcccgc cgccttcctc tcgacaaaat cccgggaact     600
ccgtctctgcc cgagcgtcgg accaggtact ggaccaaatt gctttctcag ctccttgccc     660
tgctccctag cctattccag aagctgctgc tttggagcca gctttccggg ggcctgattc     720
ctaccagatg gctagatttt gccgcaagtt acagcgccct gagagcttcg agaggacggg     780
aggaatctga cgctcccacg gtgcagaagt ctctgagtta cactgcggct ggactcttcg     840
cgaagactcg cgtcgtcagt actcttgcat tggctagagg agggactcca gtggcagtgc     900
tcgtcctcag actggaagtt aaactcaagg cccaggaaag agctttagac tctgcagcgc     960
ccactttcct cctggagcag cagctgtggg gagtggagtt gctgcccagt agccttcaag    1020
ctggtctagt ctcccaccga gaacttgact cttcatcctc tgggcctctg agcgttcaga    1080
gcttaggtaa tttcaaggta gtttcctatc tcctgaaccc ttcctacctg gactaccttc    1140
cccagttagg gctgcgctgt cagagcagcg ctggaggtgg ccagtttgtg ggtttccgaa    1200
cactaaccc  agagagctgc tatctttctg aagatggttg tcaccctcag ccgttgcggg    1260
cagagatgtc ggcaaccgcc tggagaaggt gtccgcctct ctctacagaa ggcctgccgg    1320
aaatccacca ccttcgtatg aaacggctag aattcctcca ggctaacaaa gggcaagagt    1380
tacccacccc tgaccaagat aatggctatc atagcctgga ggaggaacat aaccttctcc    1440
ggatggaccc acaacattgc acagataacc cagcacaggc ggtgtcccct gctgcagaca    1500
ggccggagcc cactgagaaa aaaccagaat tggtgattca agaagtttca cagagccccc    1560
agggaagcag tctgttttgt gaattacccg tggaaaaaga atgtgaagag gaccacacta    1620
atgcaactga cctctcagat agaggagaga gccttcctgt ttctaccaga ccagtttgta    1680
gcaacaaact gatagattat attttgggag gcgcccccag tgacttggaa gccagctctg    1740
attctgaaag tgaggattgg ggcgaggaac ctgaggacga tggctttgat agcgatggct    1800
ccctgtctga atcagacgtg gaacaggact cggaaggcct tcacctttgg aactcttttcc   1860
acagtgtaga tccttacaaa ccccaaaact ttacagccac gattcagacg ctgccagaa    1920
ttgcccccag agaccatcag attcaggga catcctggtc tggcagctgt ggtgtaggga    1980
gctgtcagga gggacccctt ccggagaccc ccgaccatag ttccggggag gaagatgact    2040
gggaaccgag tgcagatgaa gcagagaatc ttaaattgtg gaactctttc tgtcattctg    2100
aggaccccta caacctttta aattttaagg ctccttttca accgtcaggg aagaattgga    2160
aaggccgtca ggactcaaag gcctcttctg aggtcacagt ggccttctct ggccatcata    2220
```

```
ccttactttc ttgtaaggcc cagctgttag agagccaaga agataattgt ccaggctgtg    2280
ggctgggtga ggctcttgct ggagaaagat acacccatat caagagaaaa aaggtaacct    2340
tcctggaaga agttactgag tattatataa gtggtgatga ggatcgcaaa ggaccatggg    2400
aagaatttgc aagggatgga tgcaggttcc agaaacgaat tcaagaaaca gaagttgcca    2460
ttggctactg cttggccttt gagcacagag aaaaaatgtt taatagactg aggatcgagt    2520
caaaggactt actgttgtac agcaatgtta agaagtgaac agcctgcaac ccgtgcccac    2580
tctgtctctt acttgagagt ttcccttaaa aacaaacact ggcagctgtc cttggacatg    2640
tttttaaaga aacaacttgt atctagagat gcagtttgat tatttttggg taatgtgtct    2700
cattagaaac accaactccg ataatgaaga atctcttatc tgtaatcctc tcttttccta    2760
tttagttgga tgtgggtttt gtcttttga gagggtctca ctgcataatt ctgtttggcc    2820
taggtctatg tatgtagacc aggttggcct tgaagttggt atttccttgc ctctgtttcc    2880
tgtgccacca tgcccagctg gaagtgtttt taaatatcct ctgcttacct ggggtgagag    2940
tttaattttg cactttcaaa acgtttcttc tggaggcagg ggctggtctg gtttacatac    3000
aggcttcagg ccagctaggg ctatgtggtg agacctagtc ttagaggaca aacagaacaa    3060
aacagtcagg ttactgtgga aactgaggca ggaggatagg aaggtccagg tatgcctgga    3120
actcagtgaa ctctgaactc aaggccagca tggggagttt agcaagacct ttttacactc    3180
agaatggaaa aggaagctgg ggatatagct cggtagcaga ggcccctgcc tacatgtgca    3240
aggtcctggg ttcagtcccc agtactgcaa atagaaagaa aaaacattgt cttggataac    3300
tataaggttt aagcctcata gtcagttcta actcaaatta tgcatgcatt gagttcttgt    3360
gtgctttttc tgttctaaaa ttaatgggct ttatgggttt tgttttgta tgttttatg    3420 tctgttatat tttgaggtag gggattgagg cagggtctca ctgtggcctt gagctcatgg    3480
cagttttcct gcttcaactg agtgttttgg tttgtttgtg tttgtgtttt tttactttca    3540
tagatttgac ttaatgaagg caaaaacctg ttatcaacct aaaagacatt gatgtgtcac    3600
ttcagtggtg gattttctcc ctctttttttt ttttccccca gagctgagga ccaaacccag    3660
ggctttgcac ttgctaggca agcgctctac cactgagcta aatccccaaa ccaccccccc    3720
cccttttctt tttttaaaga catggtctta tatagtctag gctggcctta aactcattac    3780
ttagccaagg atggctttga aagatcctcc tgtcctcttg tttggcttgc acatggcatg    3840
tgccatacat ccagattttt ctctgtatct aggtctttt aagatatttc caaggactgc    3900
ccacaaatcc acagtgcagt actttcttga ctgggaaagc ggggttggtg tgcttttcaa    3960
aggcacacac cattatgccc agctggtctg ccaaacttaa catatttggt ttctgtgcaa    4020
actgtccatt tggaaggttt ctgtgtgttg tagtttcagt tgaatgtggc tctctgtagc    4080
tttcaagaat gggtagaaat cataaagcac tcttaagtaa tcattgcatt gtagacattt    4140 tttttttta actaggggt atttgggaga catgtcagat attcactttt gttttatgtg    4200
tcttaaaacc agtgttactt acaccctgcc tcagcactgg cacttttcaa acctgtcttg    4260
gagacactgt aaacttggat ggtgcagttc tgggttttca tgtgtaaaat gtcaactaca    4320
aaggtcaata tccaggtttg ttgtgttcta ccttatgtag agagaagcaa agcagaaagg    4380
gcagatagag cagccagaaa gtgctagtgt ccccccaaa gcgtgcttct agatagtgtg    4440
tggatcaggt gtgcttggtt tgttcagtta gcgtcacctg ttgtgcatgg ttgaggtaat    4500
gtgttaccag ttctttagtg gttacatgca caaaagagag gacctctgag tcgggtgtgg    4560
```

```
gatgagcttt ccagacctgg cagggtaaac tacctcagtt tataatctcc ctggttattt      4620
ccgtttgatg tgatctaagg tctgcctcag tggtgatgat gttcatccac acacaaggtt      4680
agtaagagtg cacgaccaga aacgttggtc ttattttga gaaccccat ttctgtgtat       4740 tttatgcacc tgcctttagt gaactccaga gtgcattaaa gagtctggtt tagtgccgtg      4800
ggaatgggct agtttagaag ctatgtttgg aaagcaggca agttgacttt aggaagaaaa      4860
gctgtgacag tgtgtagaca tttctttaa accggactgc agcttaacaa cacttgattt      4920
cagatgatta ggttttgtt tctgagaccc agcacctgta tatttaaaaa ttgttccaga       4980
ttacaccttc actatcaaat gagtaaatga ctcatgcctg cagacatgtc ctgatggtgg      5040
caagaacaga aggatctttg actgaaggag aaaaactgtc attgtcatcc cagcccccag      5100
gaaagaacac ctccaaggca ggcaggcagg caggcaggca tggtggttct agttgaatac      5160
acattcaagt cttgcagtgg tgctttagat ctgtgtagca tgtgaggctc tgtacaggtg      5220
ggggccacac ttctgagggc tgaaatgtgg caacccttta tctaacttga aatcaaaacc      5280
gtcaaatttt atttttata atttaagaaa gagttgggga atgacatttt ttgagttggc       5340
cttttcagct cagtcatttt acgtgtaacg tggagatttg atagctcaga ttatatttgt      5400
atataattat taactaatct gtaaattgta ataaatatat ttgcaattat taaaaaaaaa      5460
aaaaaaaa                                                              5468
```

<210> SEQ ID NO 4
<211> LENGTH: 698
<212> TYPE: PRT
<213> ORGANISM: Mus musculus

<400> SEQUENCE: 4

```
Met Glu Thr Gly Thr His Arg Ala Arg Lys Arg Gly Pro Arg Leu
1               5                  10                  15

Gly Ser Trp Phe Arg Leu Pro Phe Leu Arg Arg Ser His Ala Cys Ser
            20                  25                  30

Ser Glu Phe Pro Pro Pro Ser Ser Arg Gln Asn Pro Gly Asn Ser Ala
        35                  40                  45

Leu Pro Glu Arg Arg Thr Arg Tyr Trp Thr Lys Leu Leu Ser Gln Leu
    50                  55                  60

Leu Ala Leu Leu Pro Ser Leu Phe Gln Lys Leu Leu Trp Ser Gln
65                  70                  75                  80

Leu Ser Gly Gly Leu Ile Pro Thr Arg Trp Leu Asp Phe Ala Ala Ser
                85                  90                  95

Tyr Ser Ala Leu Arg Ala Ser Arg Gly Arg Glu Glu Ser Asp Ala Pro
            100                 105                 110

Thr Val Gln Lys Ser Leu Ser Tyr Thr Ala Ala Gly Leu Phe Ala Lys
        115                 120                 125

Thr Arg Val Val Ser Thr Leu Ala Leu Ala Arg Gly Gly Thr Pro Val
    130                 135                 140

Ala Val Leu Val Leu Arg Leu Glu Val Lys Leu Lys Ala Gln Glu Arg
145                 150                 155                 160

Ala Leu Asp Ser Ala Ala Pro Thr Phe Leu Leu Glu Gln Gln Leu Trp
                165                 170                 175

Gly Val Glu Leu Leu Pro Ser Ser Leu Gln Ala Gly Leu Val Ser His
            180                 185                 190

Arg Glu Leu Asp Ser Ser Ser Gly Pro Leu Ser Val Gln Ser Leu
        195                 200                 205
```

-continued

```
Gly Asn Phe Lys Val Val Ser Tyr Leu Leu Asn Pro Ser Tyr Leu Asp
        210                 215                 220
Tyr Leu Pro Gln Leu Gly Leu Arg Cys Gln Ser Ser Ala Gly Gly Gly
225                 230                 235                 240
Gln Phe Val Gly Phe Arg Thr Leu Thr Pro Glu Ser Cys Tyr Leu Ser
                245                 250                 255
Glu Asp Gly Cys His Pro Gln Pro Leu Arg Ala Glu Met Ser Ala Thr
            260                 265                 270
Ala Trp Arg Arg Cys Pro Pro Leu Ser Thr Glu Gly Leu Pro Glu Ile
        275                 280                 285
His His Arg Arg Met Arg Trp Leu Val Phe Leu Gln Pro Asn Gln Gly
        290                 295                 300
Gln Asp Leu Pro Thr Leu Asp Gln Asp Asn Gly Tyr His Ser Leu Glu
305                 310                 315                 320
Glu Glu His Asn Leu Leu Arg Met Asp Pro Gln His Cys Thr Asp Asn
                325                 330                 335
Pro Ala Gln Ala Val Ser Pro Ala Ala Asp Arg Pro Glu Pro Thr Glu
            340                 345                 350
Lys Lys Pro Glu Leu Val Ile Gln Glu Val Ser Gln Ser Pro Gln Gly
        355                 360                 365
Ser Ser Leu Phe Cys Glu Leu Pro Val Glu Lys Glu Cys Glu Glu Asp
370                 375                 380
His Thr Asn Ala Thr Asp Leu Ser Asp Arg Gly Glu Ser Leu Pro Val
385                 390                 395                 400
Ser Thr Arg Pro Val Cys Ser Asn Lys Leu Ile Asp Tyr Ile Leu Gly
                405                 410                 415
Gly Ala Pro Ser Asp Leu Glu Ala Ser Ser Asp Ser Glu Ser Glu Asp
            420                 425                 430
Trp Gly Glu Glu Pro Glu Asp Asp Gly Phe Asp Ser Asp Gly Ser Leu
        435                 440                 445
Ser Glu Ser Asp Val Glu Gln Asp Ser Glu Gly Leu His Leu Trp Asn
        450                 455                 460
Ser Phe His Ser Val Asp Pro Tyr Lys Pro Gln Asn Phe Thr Ala Thr
465                 470                 475                 480
Ile Gln Thr Ala Ala Arg Ile Ala Pro Arg Asp Pro Ser Asp Ser Gly
                485                 490                 495
Thr Ser Trp Ser Gly Ser Cys Gly Val Gly Ser Cys Gln Glu Gly Pro
            500                 505                 510
Leu Pro Glu Thr Pro Asp His Ser Ser Gly Glu Asp Asp Trp Glu
        515                 520                 525
Pro Ser Ala Asp Glu Ala Glu Asn Leu Lys Leu Trp Asn Ser Phe Cys
530                 535                 540
His Ser Glu Asp Pro Tyr Asn Leu Leu Asn Phe Lys Ala Pro Phe Gln
545                 550                 555                 560
Pro Ser Gly Lys Asn Trp Lys Gly Arg Gln Asp Ser Lys Ala Ser Ser
                565                 570                 575
Glu Val Thr Val Ala Phe Ser Gly His His Thr Leu Leu Ser Cys Lys
            580                 585                 590
Ala Gln Leu Leu Glu Ser Gln Glu Asp Asn Cys Pro Gly Cys Gly Leu
        595                 600                 605
Gly Glu Ala Leu Ala Gly Glu Arg Tyr Thr His Ile Lys Arg Lys Lys
        610                 615                 620
Val Thr Phe Leu Glu Glu Val Thr Glu Tyr Tyr Ile Ser Gly Asp Glu
```

```
                625               630               635               640
        Asp Arg Lys Gly Pro Trp Glu Glu Phe Ala Arg Asp Gly Cys Arg Phe
                        645               650               655

Gln Lys Arg Ile Gln Glu Thr Glu Val Ala Ile Gly Tyr Cys Leu Ala
                    660               665               670

Phe Glu His Arg Glu Lys Met Phe Asn Arg Leu Arg Ile Glu Ser Lys
                675               680               685

Asp Leu Leu Tyr Ser Asn Val Lys Lys
                690               695
```

```
<210> SEQ ID NO 5
<211> LENGTH: 21
<212> TYPE: DNA
<213> ORGANISM: Artificial Sequence
<220> FEATURE:
<223> OTHER INFORMATION: PCR primer

<400> SEQUENCE: 5
gatccatgga tggatggcca g                                                21

<210> SEQ ID NO 6
<211> LENGTH: 24
<212> TYPE: DNA
<213> ORGANISM: Artificial Sequence
<220> FEATURE:
<223> OTHER INFORMATION: PCR primer

<400> SEQUENCE: 6
gcatgctttg catacttctg cctg                                             24

<210> SEQ ID NO 7
<211> LENGTH: 31
<212> TYPE: DNA
<213> ORGANISM: Artificial Sequence
<220> FEATURE:
<223> OTHER INFORMATION: PCR primer G34L.Hind5S

<400> SEQUENCE: 7
tgcccaagct tcggcgatcg cacgcctgct c                                     31

<210> SEQ ID NO 8
<211> LENGTH: 32
<212> TYPE: DNA
<213> ORGANISM: Artificial Sequence
<220> FEATURE:
<223> OTHER INFORMATION: PCR primer G34L.Xho6AS

<400> SEQUENCE: 8
gaaactctcg agtaagagac agagtgggca cg                                    32

<210> SEQ ID NO 9
<211> LENGTH: 21
<212> TYPE: DNA
<213> ORGANISM: Artificial Sequence
<220> FEATURE:
<223> OTHER INFORMATION: oligonucleotide

<400> SEQUENCE: 9
gggauggaug cagguccat t                                                 21

<210> SEQ ID NO 10
<211> LENGTH: 21
<212> TYPE: DNA
<213> ORGANISM: Artificial Sequence
```

-continued

```
<220> FEATURE:
<223> OTHER INFORMATION: oligonucleotide

<400> SEQUENCE: 10
uggaaccugc auccauccct t                                              21
```